US007122668B2

(12) United States Patent
Barenholz et al.

(10) Patent No.: US 7,122,668 B2
(45) Date of Patent: Oct. 17, 2006

(54) PLATINUM COMPLEXES AND THEIR USE IN THERAPY

(75) Inventors: Yechezkel Barenholz, Jerusalem (IL); Dan Gibson, Jerusalem (IL); Yousef Najajreh, Beit Jala (IL); Elena Khazanov, Beit Shemesh (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 68 days.

(21) Appl. No.: 10/487,154

(22) PCT Filed: Aug. 21, 2002

(86) PCT No.: PCT/IL02/00687

§ 371 (c)(1),
(2), (4) Date: Nov. 17, 2004

(87) PCT Pub. No.: WO03/017998

PCT Pub. Date: Mar. 6, 2003

(65) Prior Publication Data

US 2005/0090478 A1    Apr. 28, 2005

(51) Int. Cl.
*C07F 15/00* (2006.01)
*A61K 31/28* (2006.01)
(52) U.S. Cl. .................. 544/225; 546/2; 548/101; 556/137; 514/492
(58) Field of Classification Search ................ 556/137; 514/492; 548/101; 546/2; 544/225
See application file for complete search history.

(56) References Cited

U.S. PATENT DOCUMENTS

| 4,902,797 A * | 2/1990 | Totani et al. ................. 546/11 |
| 5,026,694 A * | 6/1991 | Skov et al. .................. 514/184 |
| 2004/0097423 A1 * | 5/2004 | Siddik et al. ................. 514/18 |

FOREIGN PATENT DOCUMENTS

| EP | 0 273 315 A1 | 7/1988 |
| EP | 0727 430 A1 | 8/1996 |

OTHER PUBLICATIONS

Belluco et al., Necleophilic Constants and Substrate Discrimination Factors for Substitution Reactions of Platinum(II) Complexes, Journal of American Chemical Society, vol. 87, No. 2, pp. 241-246 (1965).*
Jamieson, E.R., et al, "Structure, Recognition, and Processing of Cisplatin-DNA Adducts", *Chem. Rev.*, pp. 2467-2498, (1999).
Kartalou, M., et al., "Recognition Of Cisplatin Adducts By Cellular Proteins", *Mutation Research*, pp. 1-21, (2001).
Gonzalez, V.M., et al., "Is Cisplatin-Induced Cell Death Always Produced By Apoptosis?" *Molecular Pharmacology*, vol. 59, No. 4, pp. 657-663, (2001).
Kartalou, M., et al., "Mechanisms of resistance to cisplatin", *Mutation Research*, pp. 23-43, (2001).
Cornelison, T.L.,et al., "Nephrotoxicity And Hydration Management For Cisplatin, Carboplatin, And Ormaplatin", *Gynecologic Oncology*, pp. 147-158, (1993).
Wong, E., et al., "Current Status Of Platinum-Based Antitumor Drugs", *Chem. Rev.* pp. 2451-2466, (1999).
Cleare, M. J., et al., "Studies On The Antitumor Activity Of Group VIII Transition Metal Complexes. Part I. Platinum (II) Complexes", *Bioinorganic Chemistry*, pp. 187-210, (1973).
Bierbach, U., et al., "Synthesis, Structure, Biological Activity, and DNA Binding of Platinum (II) Complexes of the Type trans- [$PtCl_2$ ($NH_3$) L] (L= Planar Nitrogen Base) . Effect of L and Cis/Trans Isomerism on Sequence Specificity and Unwinding Properties Observed in Globally Platinated DNA", *Inorg. Chem*, pp. 3535-3542, (1999).
Montero, E.I., et al., "Preparation and Characterization of Novel trans- [$PtCl_2$ (amine) (isopropylamine) ] Compounds: Cytotoxic Activity and Apoptosis Induction in ras-Transformed Cells", *J. Med. Chem.* pp. 4264-4268, (1999).
Coluccia, M., et al., "In vitro and in vivo antitumour activity and cellular pharmacological properties of new platinum-iminoether complexes with different configuration at the iminoether ligands", *Journal of Inorganic Biochemistry*, pp. 31-35, (1999).
Roberts, J.D., et al., "Cellular pharmacology of polynuclear platinum anti-cancer agents", *Journal of Inorganic Biochemistry*, pp. 51-57, (1999).
Kelland, L.R., et al., "Mini-review: discovery and development of platinum complexes designed to circumvent cisplatin resistance", *Journal of Inorganic Biochemistry*, pp. 111-115, (1999).
Bierbach, U., et al., "Inversion of the Cis Geometry Requirement for Cytotoxicity in Structurally Novel Platinum (II) Complexes Containing the Bidentate N, O-Donor Pyridin-2-yl-acetate", *Inorganic Chem*, pp. 1882-1890, (2000).
Hollis, L.S., et al., Chemical and Biological Properties of a New Series of cis-Diammineplatinum (II) Antitumor Agents Containing Three Nitrogen Donors: cis- [Pt ($NH_3$) $_2$ (N-donor) Cl] $^+$, *J. Med. Chem.*, pp. 128-136, (1989).
Kelland, L.R., et al., "Preclinical antitumor evaluation of bis-acetato-ammine-dichloro-cyclohexylamine platinum (IV) : an orally active platinum drug", *Cancer Research*, pp. 2581-2586, (1993).
Loh, S.Y., et al., "Reduced drug accumulation as a major mechanism of acquired resistance to cisplatin in a human ovarian carcinoma cell line: circumvention studies using novel platinum (II) and (IV) ammine/amine complexes", *Brit.J. Cancer*, pp. 1109-1115, (1992) .
Goddard, P.M., et al, " Novel Trans Platinum Complexes: Comparative *in Vitro* and *in Vivo* Activity Against Platinum-Sensitive and Resistant Murine Tumours", *Anticancer Research*, pp. 33-38, (1996).

(Continued)

*Primary Examiner*—Porfirio Nazario-Gonzalez
(74) *Attorney, Agent, or Firm*—nath & Associates PLLC; Gary M. Nath; Susanne M. Hopkins

(57) ABSTRACT

The present invention concerns novel platinum complexes in which at least one of the amine ligand is a non-planar heterocyclic aliphatic amine. The platinum complexes may be in a trans or cis configuration and were found to posses therapeutic activites. Thus, the present concerns novel platinum complexes, pharmaceutical compositions comprising them and other uses thereof.

51 Claims, 8 Drawing Sheets

OTHER PUBLICATIONS

Behrens, B.C., et al., "Characterization of a cisdiamminedichloroplatinum (II) -resistant human ovarian cancer cell line and its use in evaluation of platinum analogues", *Cancer Research*, pp. 414-418, (1987).

Gorodetsky, R., et al., "Combination of cisplatin and radiation in cell culture: Effect of duration of exposure to drug and timing of irradiation", *Int. J. Cancer*, pp. 635-642, (1998).

Gorodetsky, R., et al., "Sub-additive effect of the combination of radiation and cisplatin in cultured murine and human cell lines", *Israel J. Med. Science*, pp. 95-100, (1995).

Cory, A.H., et al., "Use of an Aqueous Soluble Tetrazolium/ Formazan Assay for Cell Growth Assays in Culture", *Cancer Communications*, pp. 207-212, (1991).

Lindauer, E., et al., "Cellular Distribution and Cellular Reactivity of Platinum (II) Complexes", *Biochemical Pharmacology*, pp. 7-14, (1996).

Zuidam, N., et al., "Lamellarity of cationic liposomes and mode of preparation of lipoplexes affect transfection efficiency", *Biochimica ET Biophysica Acta*, pp. 207-220, (1999).

Chen, S.E., et al., "DOTAP cationic liposomes prefer relaxed over supercoiled plasmids", *Biochimica ET Biopysica Acta*, pp. 176-188, (2000).

Reid, S., et al., "Combined Hoechst 33342 and merocyanine 540 staining to examine murine B cell cycle stage, viability and apoptosis", *Journal of Immunological Methods*, pp. 43-54, (1996).

Holford, J., et al., "Chemical, biochemical and pharmacological activity of the novel sterically hindered platinum co-ordination complex, cis- [amminedichloro (2-methylpyridine) ] platinum (II) (AMD473)", *Anti-Cancer Drug Design*, pp. 1-18, (1998).

Thornberry, N.A, et al., "Caspases: Enemies Within", *Science*, pp. 1312-1316, (1998).

Villa, P., et al., "Caspases and caspase inhibitors", *Science*, pp. 388-393, (1997).

Ciesielska, E., et al., "Dna Damage And Apoptosis Induction In L1210 Cells By *Cis*-Diamminedichloroplatinum (II) And Its New Aminoflavone Analogue" *Cellular & Molecular Biology Letters*, pp. 441-450, (2000).

Lui, W., et al., "Endothelial Cell Apoptosis Is Inhibited By A Soluble Factor Secreted By Human Colon Cancer Cells", *Int. J. Cancer*, pp. 26-30, (2001).

Barenholz, Y., et al., "Quality Control Assays In The Development And Clinical Use Of Liposome-Based Formulations", $2^{nd}$ Ed., G. Gregoriadis (Ed.) *CRC Press*, Boca Raton, Ch.29, vol. 1, pp. 527-616, (1993).

XP-001117912: Nguyen, H., et al, "1H-NMR Spectra And Structure Of Some Pt (II)—Complexes Containing Quinoline", *Vietnam Journal of Chemistry*, vol. 39 No. 4, pp. 111-114, (2001).

XP-001119544: Tran, T., et al., "Synthesis and Biological Effects of some complex cis-diamine Compounds of Platinum (II) containing Piperidine or Morpholine and some other Amines", *Tap Chi Duoc Hoc*, No. 6, pp. 6-8, (2001).

XP 001117911: Tran, T., et al., "syntheses and properties of some mixed cis-diamine pt(II) complexes containing piperidine and aromatic amines", *Vietnam Journal of Chemistry*, vol. 39, No. 3, pp. 99-102, (2001).

XP-001119543: Tran T., et al., "synthesis and properties of some mixed cis-diamine of platinum (II) containing quinoline", *Vietnam Journal of Chemistry*, vol. 35, No. 2, pp. 21-23, (1997).

XP-001119659: Ivanova, N., et al., "Coordination Abilities Of Piperazine In Platinum (II), Platinum (IV), And Palladium (II) Complexes", *Russian Journal of Coordination Chemistry*, vol. 19, No. 12, pp. 856-863, (1993).

XP-001119636: Cattalini, L, et al., "The cis-and trans-Effects of Cyanide in Substitutuion at Platinum (II)", *Journal of the Chemical Society, Dalton Transactions*, pp. 233-236, (1993).

XP-002220406: Wong, E., et al., "Current Status of Platinum-Based Antitumor Drugs", *Chem. Rev.*, pp. 2451-2466, (1999).

\* cited by examiner

PLATINUM COMPLEXES AND THEIR USE IN THERAPY

FIELD OF THE INVENTION

The present invention relates to novel platinum complexes and their uses.

BACKGROUND OF THE INVENTION AND PRIOR ART

Cisplatin, cis-[PtCl$_2$(NH$_3$)$_2$] is one of the three most widely used clinical agents in the treatment of a variety of solid tumors[1]. It is believed to kill tumor cells by binding irreversibly to the DNA, mainly to two adjacent guanines on the same strand, inducing a kink in the DNA that is recognized by cellular proteins that bind the cisplatin-modified DNA[2]. It is the Pt-DNA adducts that are responsible for the induction of apoptosis and eventual cell death[3]. Despite its efficacy in the treatment of various neoplastic diseases, including testicular and ovarian tumors, it's clinical utility is restricted by its low solubility, toxicity and especially tumor resistance[4]. Second generation drugs such as carboplatin (Pt(CBDCA)(NH$_3$)$_2$, CBDCA=1,1-cyclobutanedicarboxylate) exhibit reduced nephrotoxicity but fail to overcome the tumor resistance probably due to the fact that they form the same spectrum of DNA adducts as does cisplatin[5].

Overcoming the resistance is one of the major goals in the development of novel platinum drugs and hence new compounds that deviate from the classic structure-activity relationship (SAR) have been designed, synthesized and screened[6]. The SAR, first formulated by Cleare and Hoeschele, influenced medicinal chemists to direct their efforts to the preparation of neutral platinum(II) complexes with two inert ligands in the cis configuration and two semi-labile leaving groups[7].

It was generally accepted that a cis configuration of the two leaving groups is essential for anti-tumor activity of cis-diaminedichloroplatinum (cis-DDP). This was the situation for more than two decades until Farrell et. al have reported that replacing one or both NH$_3$ ligands in trans-PtCl$_2$(Am$_1$)(Am$_2$), wherein Am$_1$, Am$_2$=NH$_3$, or planar amine ligands such as quinoline, thiazole, pyridine or benzothiazole, (e.g. trans-[PtCl$_2$(NH$_3$)(pyridine)], trans-[PtCl$_2$(NH$_3$)(thiazole)], trans-[PtCl$_2$(NH$_3$)(quinoline)], and trans-[PtCl$_2$(NH$_3$)(benzothiazole)]) substantially enhances the cytotoxicity of the trans geometry[8]. Nguyen, H. D. et al. *Vietnam J. of Chem.* (2001) 39(4), 111–114 describe the synthesis of cis-PtCl$_2$ complexes containing quinoline and primary and secondary amines and discuss their $^1$H-NMR spectra. Tran, T. D. et al. *Tap Chi Duoc Hoc* (2001) 6, 6–8 describe cis-PtCl$_2$ complexes containing two amine-containing ligands, one being an aromatic pyridine or benzylamines and the other a aliphatic cyclic amine (morpholine or piperidine) and discuss the complexes IR and Raman spectra. Tran T. D. et al. *Vietnam J. of Chem.* (2001) 39(3), 99–102 describe the synthesis of cis-PtCl$_2$ complexes containing piperidine and aromatic amine or an amine substituted with an aromatic amine, their IR, Raman and UV spectra. Furthermore, the complexes were tested for cell cytotoxicity on human liver cancer cells. Tran, T. D. et al. *Tap Chi Duoc Hoc* (*Vietnam J. of Chem.*) (1997) 35(2), 21–23 describe the synthesis of cis-PtCl$_2$ complexes containing guinoline and an amine selected from morpholine, cyclohexylamine, piperidine or benzylamine, their UV and IR spectra and their biological activity for reducing the germination of kernels. Jonson Matthey Pub. Ltd. Co. EP-A-0727430 (1996) describes cis-Pt complexes of formula Pt(X)(Z)(A)$_2$ and their activity against cancer cells. A is a leaving group (e.g. halogen, hydroxy, carboxylate, or together form a bi-dentate carboxylate, or sulphate) and X is NH$_3$ or mono- or dialkyl substituted NH$_3$. Z is a substituted amine, preferably a 5- or 6-membered monocyclic or an 8–10 membered polycylic amine, especially substituted pyridine or bycylic amine where the amine is coordinated through the nitrogen atom. Ivanova, N. A. et al. *Russian J. Coord. Chem.* (1993) 19(12) 856–863 describe the synthesis of PtX$_2$ complexes with piperazine, where X may be Cl or Br. The synthesized complexes were analyzed with vibrational spectroscopy for elucidating the piperazine conformation. Cattalini, L. et al. *J. Chem. Soc. Dalton Transactions* (1993) 233–236 describe cis and trans PtCl$_2$ complexes containing two amine ligands, the amine chosen from pyridine, substituted pyridine, morpholine, piperidine and dimethylamine. Shionogi & Co. EP-A-0273315 (1988) disclose cis-PtX$_2$(NH$_3$)(Am) complexes. X maybe Cl, I, nitro or a cyclic moiety and Am is a substituted C$_{2-7}$N and their antitumor activity. Wong et al. *Chem. Rev.* (1999) 99(9), 2451–2466 review platinum-based antitumor drugs mentioning cis-Pt complexes.

In addition, Navarro-Ranniger and co-workers demonstrated that trans-PtCl$_2$[NH$_2$CH(CH$_3$)$_2$][NH(CH$_3$)$_2$] has interesting pharmacological properties[9] and Natile et. al. reported that trans-PtCl$_2$(iminoether)$_2$ is also active against several human cancer lines[10]. Another example of a non-classical complex that is in phase 2 of clinical trials is the trinuclear Pt complex BBR3464 that is a quadruply charged cation[11].

The importance of the non-classical platinum compounds stems from the fact that they were designed to form a spectrum of DNA adducts that is distinct from that formed by cisplatin and carboplatin and hence they can circumvent acquired Pt resistance[12].

Generally, trans-diaminedichloroplatinum(II) analogues have lower solubility in aqueous solution than their cis counterparts, resulting in limited bioavailability. One way of increasing the aqueous solubility is by adding a charge to the complex. Farrell et al. have put some effort in overcoming the poor water solubility of compounds of the type trans-[PtCl$_2$(NH$_3$)(Am$_1$)](Am$_1$=planar ligand), while retaining the trans orientation of the NH$_3$ and the planar ligand and electroneutralilty of the square-planar entity. The trans-platinum complex trans-[PtCl(PyAc—N,O)(NH$_3$)] (PyAc=pyridin-2-yl acetate, N-donors are trans) and its cis isomer were synthesized and the trans isomer have shown improved solubility (ca. 4–5 mmol L$^{-1}$) in water, compared to analogous complexes trans-[PtCl$_2$(NH$_3$)(Am$_1$)] (Am$_1$=planar ligand)[13]. On the other hand, the cationic charges of the platinum complexes prepared by Farrell et al. and also by Hollis et al. reside on the metal center and result from the substitution of one or the anionic chloride ligands by a neutral ligand[14].

SUMMARY OF THE INVENTION

The present invention concerns, according to a first of its aspects, novel Platinum complexes (Pt-complexes) in the trans configuration having the general formula (I):

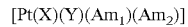

wherein:

X and Y, which may be the same or different, represent a halogen, carboxylate, phosphate or sulphate group;

Am$_1$ represents an amine selected from ammonia, a primary amine, a secondary amine, a non-planar heterocyclic aliphatic amine or a heterocyclic aromatic amine; and Am$_2$ represents a non-planar heterocyclic aliphatic amine, wherein the following compounds are excluded trans-[Pt(piperidine)$_2$Cl$_2$] and trans-[Pt(morpholine)$_2$Cl$_2$].

The Pt-complex of the invention may be in the form of a dimer in which each monomeric unit is a Pt-complex as defined, bound to the other Pt-complex, independently, through the Am$_1$ or through the Am$_2$ or through a linker connected to said Am$_1$ or Am$_2$.

According to another aspect, the invention concerns pharmaceutical compositions comprising a pharmaceutically acceptable carrier and as an active ingredient a therapeutically effective amount of a Pt complex of the general formula:

[Pt(X)(Y)(Am$_1$)(Am$_2$)]

wherein:
X and Y, which may be the same or different, represent a halogen, carboxylate, phosphate or sulphate group;
Am$_1$ represents an amine selected from ammonia, a primary amine, a secondary amine, a non-planar heterocyclic aliphatic amine or a heterocyclic aromatic amine; and
Am$_2$ represents a non-planar heterocyclic aliphatic amine, with the proviso that when said complex is in a cis configuration, Am$_1$ and Am$_2$ cannot represent simultaneously piperidine.

The invention also concerns a method for achieving a therapeutic effect, the method comprising administering to a subject in need an amount of a platinum complex, the amount being sufficient for achieving said therapeutic effect and the Pt complex comprises the general formula (I):

[Pt(X)(Y)(Am$_1$)(Am$_1$)]     (I)

wherein:
X and Y, which may be the same or different, represent a halogen, carboxylate, phosphate or sulphate group;
Am$_1$ represents an amine selected from ammonia, a primary amine, a secondary amine, a non-planar heterocyclic aliphatic amine or a heterocyclic aromatic amine; and
Am$_2$ represents a non-planar heterocyclic aliphatic amine, with the proviso that when said complex is in a cis configuration, Am$_1$ and Am$_2$ cannot represent simultaneously piperidine.

According to yet another aspect the invention concerns a platinum complex of the general formula (I):

[Pt(X)(Y)(Am$_1$)(Am$_2$)]     (I)

wherein:
X and Y, which may be the same or different, represent a halogen, carboxylate, phosphate or sulphate group;
Am$_1$ represents an amine selected from ammonia, a primary amine, a secondary amine, a non-planar heterocyclic aliphatic amine or a heterocyclic aromatic amine; and
Am$_2$ represents a non-planar heterocyclic aliphatic amine;
wherein the following compounds are excluded:
cis-[PtCl$_2$(quinoline)(piperidine)]; cis-[PtCl$_2$(piperidine)(pyridine)]; cis-[PtCl$_2$-(piperidine)(o-CH$_3$—C$_6$H$_4$—NH$_2$)]; cis-[PtCl$_2$(piperidine)(p-CH$_3$—C$_6$H$_4$—NH$_2$)]; cis-[PtCl$_2$(morpholine)(pyridine)]; cis-[PtCl$_2$(morpholine)(o-CH$_3$—C$_6$H$_4$—NH$_2$)]; cis-[PtCl$_2$(morpholine)(p-CH$_3$—C$_6$H$_4$—NH$_2$]; cis-[PtCl$_2$(piperidine)(aniline)]; cis-[PtCl$_2$(piperidine)(o-CH$_3$O—C$_6$H$_4$—NH$_2$)]; cis-[PtCl$_2$(piperidine)(p-C$_2$H$_5$OC$_6$H$_4$—NH$_2$)]; cis-[PtCl$_2$(quinoline)(cyclohexylamine)]; cis-[PtCl$_2$(quinoline)(morpholine)]; cis-[PtCl$_2$(quinoline)(piperidine)]; cis-[PtBr$_2$(piperazine)(piperazine); cis-[PtCl$_2$(piperazine)(piperazine)]; cis-[PtCl$_2$(piperidine)(piperidine)]; cis-PtCl$_2$(morpholine)(morpholine)]; cis-[PtCl$_2$(pyrrolidine)(NH$_3$)]; cis-[PtI$_2$(pyrrolidine)(NH$_3$)]; cis-{PtICl(pyrrolidine)(NH$_3$)]; cis-[PtCl$_2$(piperidine)(NH$_3$)]; cis-[PtI$_2$(piperidine)(NH$_3$)]; cis-[PtCl$_2$(piperidone)(NH$_3$)]; cis-[PtI$_2$(piperidone)(NH$_3$)]; cis-[PtICl(piperidone)(NH$_3$)]; cis-[PtCl$_2$(3-hydroxypyrrolidine(NH$_3$)]; cis-[PtI$_2$(3-hydroxypyrrolidine)(NH$_3$)], cis-[PtClI(3-hydroxypyrrolidine)(NH$_3$), trans-[Pt(piperidine)$_2$Cl$_2$] and trans-[Pt(morpholine)$_2$Cl$_2$].

DETAILED DESCRIPTION OF THE INVENTION

Figure 1A:
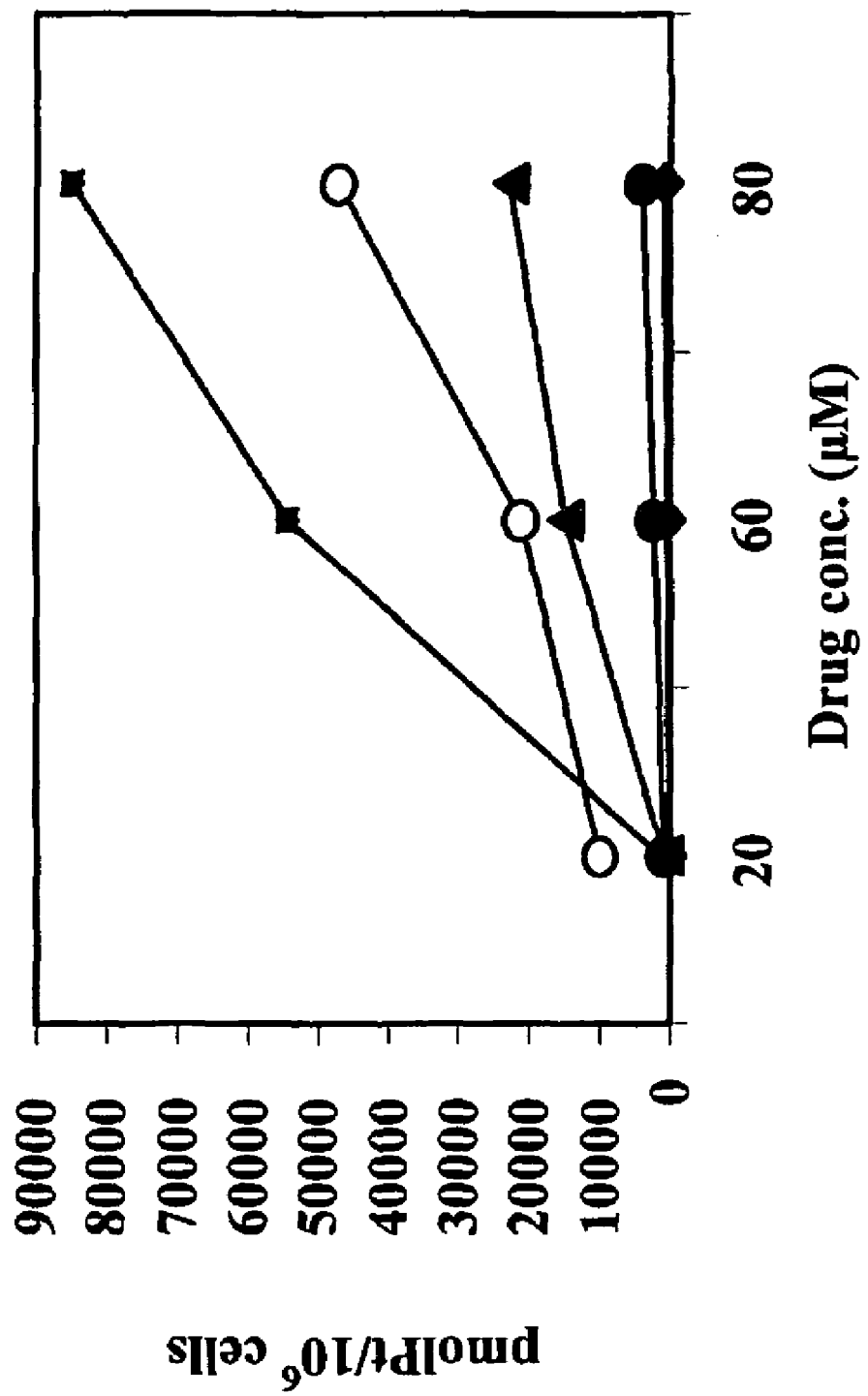
FIGS. 1A–1B show uptake by C-26 cancer cells (FIG. 1A) or OV-1063 cancer cells (FIG. 1B) of cisplatin (-?-); transplatin (-|-); trans-[(PtCl$_2$)(4-picoline)(piperidine)](-^-); trans-[PtCl$_2$)(4-picoline)(piperazine)].HCl (-|-) and trans-[PtCl$_2$(NH$_3$)(piperidino-piperidine)].HCl (-o-). The Pt content was determined by Atomic Absorption Spectroscopy (AAS).

The present invention is based on the surprising finding that inclusion of a non-planar heterocyclic aliphatic amine ligand into a Pt-complex, have therapeutic advantages, e.g. in the field of cancer treatment. The Pt-complex according to the invention includes at least one non-planar heterocyclic amine ligand, which is flexible and has a hydrogen bond donor that can interact with other substances, such as with DNA, to form lesions. The ligand is also bulky enough to affect the kinetics and the cytotoxicity of the resulting complex.

Thus, the present invention provides, according to one of its aspects, a platinum complex (Pt-complex) of the general formula (I):

$$[Pt(X)(Y)(Am_1)(Am_2)] \qquad (I)$$

wherein:

X and Y, which may be the same or different, represent a halogen, carboxylate, phosphate or sulphate group;

$Am_1$ represents an amine selected from ammonia, a primary amine, a secondary amine, a non-planar heterocyclic aliphatic amine or a heterocyclic aromatic amine; and $Am_2$ represents a non-planar heterocyclic aliphatic amine, with the proviso that when said complex is in a cis configuration, $Am_1$ and $Am_2$ cannot represent simultaneously piperidine.

The term "Pt-complex" as used herein refers in its broadest sense to any Pt-complex comprising two amine-containing ligands, wherein at least one ligand is a non-planar heterocyclic aliphatic amine. These complexes include both the cis and trans regioisomers (with the proviso that when the complex is in a cis configuration, the two amine ligands do not represent simultaneously piperidine). The Pt-complex may include Pt(II) coordinated or Pt(IV) coordinated as the metal center. In addition, the Pt-complex may be in the form of a dimer in which each monomeric unit is a Pt-complex as defined above, bound to the other Pt-complex, independently, through one of its amine ligands, directly, or via a linker connected to said $Am_1$ or $Am_2$, the two amine ligands may also form together a cyclic ring, such as a piperizine ring coordinated with each Pt metal through a nitrogen atom.

According to a preferred embodiment, X and Y are the same or different and represent chloride or iodide and more preferably, X and Y both represent a chloride.

According to the invention $Am_1$ may represent ammonia; a primary amine such as, without being limited thereto, methylamine, ethylamine, n-propylamine, isopropylamine, n-butylamine, n-hexylamine, n-heptylamine or n-nonylamine; a secondary amine such as, without being limited thereto, dimethylamine, diethylamine, dipropylamine, dibutylamine; a non-planar heterocyclic aliphatic amine, such as, without being limited thereto, piperazine, 2-methylpiperazine, piperidine, 2-, 3-, or 4-hydroxypiperidine, 4-piperidino-piperidine, pyrrolidine, 4-(2-hydroxyethyl)piperazine and 3-aminopyrolidine; or a heterocyclic aromatic amine, such as, without being limited thereto, pyridine, 2-, 3-, or 4-aminopyridine, 2-, 3-, or 4-picoline, quinoline, 3-, or 4-aminoquinoline, thiazole, imidazole, 3-pyrroline, pyrazine, 2-methylpyrazine, 4-aminoquinaldine.

The $Am_2$ according to the invention is a non-planar heterocyclic amine such as, without being limited thereto, piperazine (referred to herein, at times, by the abbreviation "pz"), 2-methylpiperazine, piperidine (referred to herein, at times, by the abbreviation "pip"), 2-, 3-, or 4-hydroxypiperidine, 4-piperidino-piperidine (referred to herein, at times, by the abbreviation "pip-pip"), pyrrolidine, 4-(2-hydroxyethyl)piperazine and 3-aminopyrolidine.

As indicated above, the Pt-complexes of the invention refer to all regioisomers of the complexes having the general formula (I) identified above. According to one aspect, the Pt-complexes are in the trans configuration. Specific examples include:

trans-[PtCl$_2$(NH$_3$)(piperidine)];
trans-[PtCl$_2$(NH$_3$)(4-hydroxypiperidine)];
trans-[PtCl$_2$(NH$_3$)(4-piperidino-piperidine)];
trans-[PtCl$_2$(NH$_3$)(4,4'-bipiperidine)];
trans-[PtCl$_2$(4-picoline)(piperidine)];
trans-[PtCl$_2$(piperidine)$_2$];
trans-[PtCl$_2$(NH$_3$)(piperazine)].HCl;
trans-[ptcl$_2$(isopropylamine)(piperazine)].HCl;
trans-[PtCl$_2$(n-butylamine)(piperazine)].HCl;
trans-[PtCl$_2$(n-nonylamine)(piperazine)].HCl
trans-[PtCl$_2$(piperidine)(piperazine)].HCl;
trans-[PtCl$_2$(4-picoline)(piperazine)].HCl;
trans-[PtCl$_2$(piperazine)(piperazine)].HCl;
trans-[PtCl$_2$(NH$_3$)[4-(2-hydroxyethyl)piperazine)].HCl;

According to yet another aspect, the complexes are in a cis configuration. Specific cis isomers include, without being limited thereto, cis-[PtCl$_2$(NH$_3$)(piperidine)] or cis-[PtCl$_2$(NH$_3$)(piperazine)].HCl.

As indicated above, the non-planar heterocyclic amine ligand is flexible and has a hydrogen bond donor that can interact with the DNA to form lesions and is bulky enough to affect the kinetics and the cytotoxicity of the resulting complex. In addition, some of the amine ligands such as piperazine confer the complex with a positive charge, thus ensuring adequate aqueous solubility and rapid interaction of the complex with polyanionic molecules, such as the DNA.

The complex may also be in the form of a dimer. Accordingly, two Pt-complexes are associated via a valance bond, a cyclic ring formed between the amine substituent of each Pt-complex (e.g. forming together a piperazine ring) or by a linker connected to the $Am_1$ or the $Am_2$ ligands of each complex. Non-limiting examples of linkers include short polyethyleneglycol chains (PEG), short diaminoalkanes (e.g. 1,6-diaminohexane, 1,8-diaminooctane). A specific example for a linker is 4,7,10-trioxa-1,13-tridecane chain and one specific dimer in which the two Pt-complexes are associated by this linker is Bis-[{trans, trans-(PtCl$_2$piperazine)$_2$}(4,7,10-trioxa-1,13-tridecanediamine)].2HCl.

The invention also concerns pharmaceutical compositions comprising a pharmaceutically acceptable carrier and as an active ingredient a therapeutically effective amount of the Pt-complex of the invention as defined above.

The Pt-complex of the present invention is administered and dosed in accordance with good medical practice, taking into account the clinical condition of the individual patient, the site and method of administration, scheduling of administration, patient age, sex, body weight and other factors known to medical practitioners. The therapeutically "effective amount" for purposes herein is thus determined by such considerations as are known in the art. The amount must be effective to achieve improvement including, but not limited to, improved survival rate or more rapid recovery from a disease state treated with the active ingredient of the invention, or improvement or elimination of symptoms associated with the disease state and other indicators as are selected as appropriate measures by those skilled in the art.

The effective amount is typically determined in appropriately designed clinical trials (dose range studies) and the person versed in the art will know how to properly conduct such trials in order to determine the effective amount. As generally known, an effective amount depends on a variety of factors including the affinity of the Pt-complex to, for example, DNA, to form a Pt-DNA adduct, the Pt-complex's distribution profile within the body, a variety of pharmacological parameters such as half life in the body, on undesired side effects, if any, on factors such as age and gender, etc.

Many modes of administration may be employed for the delivery of Pt-complex, and these will necessitate the use of different carriers, adjuvants, elixirs, and the like, as known in the art.

Evidently, the pharmaceutically acceptable carriers employed according to the invention generally refer to inert, non-toxic solid or liquid fillers, diluents or encapsulating material to the extent that they do not hinder or interfere with the therapeutic effect desired of the Pt complex and do not react with the Pt-complex of the invention.

The Pt-complex can be administered orally, subcutaneously or parenterally including intravenous, intraarterial, intramuscular, intraperitoneally and intranasal administration as well as intrathecal and by infusion techniques. Further, the Pt-complex can be suspended in chlorofluorocarbon or hydrofluorocarbon propellants for delivery via inhaler to the lungs. Alternatively, the Pt-complex can be formulated in a matrix (lactose, etc.) or carrier (e.g., liposomes, etc.), which will allow delivery either orally, sublingually or by suppository.

The doses may be single doses or multiple doses over a period of several days. The treatment generally has a length proportional to the length of the disease process and active ingredient effectiveness and the patient species being treated. Further, the administration of Pt-complex of the present invention can be intermittent, or at a gradual, or continuous, constant or controlled rate to a patient. The host or patient for the therapeutic treatment using the platinum compounds described herein generally are mammalian, such as humans, dogs, and rodents, and so forth.

When administering the Pt-complex of the invention parenterally, it will generally be formulated in a unit dosage injectable form (solution, suspension, emulsion). The pharmaceutical formulation suitable for injection includes sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, lipid polyethylene glycol and the like), suitable mixtures thereof and vegetable oils. Nonaqueous vehicles such as cottonseed oil, sesame oil, olive oil, soybean oil, corn oil, sunflower oil, or peanut oil and ester, such as isopropyl myristate, may also be used as solvent systems for the Pt-complex of the invention.

Additionally, various additives which enhance the stability, sterility and isotonicity of the Pt-complex containing compositions of the invention, including antimicrobial preservatives, antioxidants and buffers can be added. Prevention of the action of microorganisms can be ensured by various antibacterial and antifungal agents, for example, parabens, chlorobutanol, phenol, sorbic acid and the like.

The pharmaceutical composition of the invention may also be administered orally to the subject in need. Conventional methods such as administering the active compound in tablets, suspensions, solutions, emulsions, capsules, powders, syrups and the like are usable. Known techniques which deliver it orally or intravenously and retain the biological activity thereof are preferred.

According to one preferred embodiment, the Pt-complex of the invention is is entrapped by or loaded onto a liposome. The term "liposome" as used herein includes all spheres or vesicles of liposome-forming lipids that may spontaneously or non-spontaneously vesiculate, for example, phospholipids which are glycerides where at least one acyl group is replaced by a complex phosphoric acid ester.

The term "loaded" or "entrapped" means either entrapped within the interior of the liposome, exposed or present at the surface of the liposome, embedded in the liposome's membrane.

The liposomes according to the invention may be formed from any known liposome forming lipids. As used herein, the term "liposome-forming lipid" denotes any physiologically acceptable amphipathic substance that contains groups with characteristically different properties, e.g. both hydrophilic and hydrophobic properties or a mixture of such molecules, and which upon dispersion thereof in an aqueous medium form liposomal vesicles. The liposomes may be comprised of a single amphipathic substance or from a mixture of such substances.

The amphipathic substance includes, inter alia, phospholipids, sphingolipids, glycolipids, such as cerebrosides and gangliosides, PEGylated lipids, and sterols, such as cholesterol and others. Any commonly known liposome-forming lipids are suitable for use by the method of the present invention. The source of the lipid or its method of synthesis is not critical: any naturally occurring lipid, with and without modification, or a synthetic phosphatide can be used.

Preferred liposome-forming amphipathic substances are natural, semi-synthetic or fully synthetic, molecules; negatively or positively charged lipids, phospholipids or sphingolipids, optionally combined with a sterol, such as cholesterol; and/or with lipopolymers, such as PEGylated lipids.

The liposomes employed by the invention can be "tailored" to the requirements of any specific reservoir including various biological fluids, which maintain their stability without aggregation or chromatographic separation, and thereby remain well dispersed and suspended in the injected fluid. The fluidity in situ changes due to the composition, temperature, salinity, bivalent ions and presence of proteins. The liposomes can be used with or without any other solvent or surfactant.

A preferred phospholipid combination according to the invention includes a mixture of (HSPC):cholesterol: $PEG^{2000}$-DSPE (HSPC referring to hydrogenated soybean phosphatidylcholine while $PEG^{2000}$-DSPE refers to Di-stearoyl-phosphatidyl-ethanolamine to which $PEG^{2000}$ is bound to the head group) or alternatively, diacylglycol PEG (having two stearoyl acyl chains) or cholesterol-PEG.

The composition of the invention is intended for achieving a therapeutic effect, the therapeutic effect involving the formation of an adduct between the Pt complex of the invention and a nucleic acid molecule such as a DNA. The therapeutic effect may comprise inhibition of undesired cell proliferation or for induction of apoptosis of undesired cells.

Thus, the composition of the present invention may be used for the treatment or prevention of a disease state, the disease state being associated with undesired cell proliferation. The term "treatment or prevention" as used herein refers to the administering of a therapeutic amount of the composition of the invention which is effective to ameliorate undesired symptoms associated with the disease state, to prevent the manifestation of such symptoms before they occur, to slow down the progression of the disease (As may be evident from rate of proliferation of a diseased tissue), slow down the deterioration of symptoms, to enhance the onset of remission period, slow down the irreversible damage caused in the progressive chronic stage of the disease (for example, in autoimmune diseases), to delay the onset of said progressive stage, to lessen the severity or cure the disease, to improve survival rate or to achieve a more rapid recovery, or to prevent the disease form occurring or a combination of two or more of the above.

Thus, the instant invention also concerns a method for achieving a therapeutic effect, the method comprising administering to a subject in need an amount of a platinum complex according to the invention, the amount being sufficient for achieving said therapeutic effect. According to one embodiment, the Pt-complex of the invention is used as an anti-cancer agent.

The invention will now be further explained by the following non-limiting examples. While the foregoing description describes in detail only a few specific embodiments of the invention, it will be understood by those skilled in the art that the invention is not limited thereto and that other variations in form and details may be possible without departing from the scope and spirit of the invention as defined by the claims, which are to be read as included within the disclosure of the specification.

DETAILED DESCRIPTION OF SPECIFIC EMBODIMENTS

EXAMPLE 1

Chemical Synthesis (1) Synthesis of Piperidine-containing Pt Complexes

General Procedure for Preparing trans-[PtCl$_2$(NH$_3$)(R)]

In the following description R refers to any one of the following piperidine derivatives: piperidine, 4-hydroxypiperidine, 4-piperidino-piperidine, 1,4'-bispiperidine. For further reference, the derivatives obtained will be identified by a reference number appearing in brackets.

Cis-diamminedichloroplatinum(II) (300 mg, 1 mmol) was suspended in 30 mL of double distilled water DDW. Two equivalents (eq.) of the piperidine derivative were added, and the suspension was heated to 85° C. for 3 h. During this time the yellow suspension turned to a colorless clear solution (in some cases a black precipitate was formed). The reaction mixture was cooled to r.t., filtered, and 1 mL of concentrated HCl was added dropwise. The temperature was elevated to 90° C. for 6 h, during which the yellow product, trans-[PtCl$_2$(NH$_3$)(piperidine derivative)], precipitated. The reaction mixture was allowed to stand at r.t. for 4 h, after which the yellow product was collected by filtration and washed with 40 mL of DDW, 10 mL of EtOH, and 40 mL of diethyl ether.

Trans-[PtCl$_2$(NH$_3$)(piperidine)] (1): Yield 86.9%. Anal. (C$_5$H$_{14}$Cl$_2$N$_2$Pt) C,H,N. $^{195}$Pt NMR($\delta$, DMF): −2167 ppm.

Trans-[PtCl$_2$(NH$_3$)(4-hydroxypiperidine)] (2): Yield 80.0%. Anal. (C$_5$H$_{14}$Cl$_2$N$_2$OPt) C,H,N. $^{195}$Pt NMR($\delta$, DMF): −2172 ppm.

Trans-[PtCl$_2$(NH$_3$)(4-piperidino-piperidine)] (3): Yield 78.5%. Anal. (C$_{10}$H$_{24}$Cl$_3$N$_3$Pt) C,H,N. $^{195}$Pt NMR($\delta$, H$_2$O): −2170 ppm.

Trans-[PtCl$_2$(NH$_3$)(4,4'-bipiperidine)] (4): Yield 85.9%. Anal. (C$_{10}$H$_{24}$Cl$_3$N$_3$Pt) C,H,N. $^{195}$Pt NMR($\delta$, H$_2$O): −2175 ppm.

Procedure for Preparing trans-[PtCl$_2$(4-picoline)(piperidine)] (5)

K$_2$PtCl$_4$ (200 mg, 0.482 mmol) was dissolved in 30 mL of DDW. 4-Picoline (2.5 eq., 117.3 µL; 1.2 mmol) was added and the mixture stirred overnight at r.t. The yellow precipitate, cis-[PtCl$_2$(4-picoline)$_2$] [$^{195}$Pt NMR(DMF)=−1964 ppm], was collected by filtration and washed with 50 mL of DDW and 40 mL of diethyl ether. Cis-[PtCl$_2$(4-picoline)$_2$] (226 mg, 0.5 mmol) was suspended in 40 mL of DDW with 2 eq. of piperidine (99 µL, 1 mmol), and the suspension was heated to 80° C. for 3 h. The solution turned clear and colorless with some formation of a black precipitate The reaction mixture was allowed to cool to r.t. and the precipitated material was filtered off. To the colorless filtrate, 1 mL of concentrated HCl was added and the mixture was heated to 90° C. The heating was maintained for 6 h during which a yellow precipitate was formed. The reaction mixture was allowed to cool to r.t., and the precipitate (180 mg) was collected and washed with 50 mL of DDW, 10 mL of EtOH, and 30 mL of diethylether.

Yield: 81%. Anal. (C$_{11}$H$_{18}$C$_{12}$N$_2$Pt): C,H,N. $^{195}$Pt NMR ($\delta$, DMF): −2087 ppm.

Procedure for Preparing Trans-[PtCl$_2$(piperidine)$_2$] (6)

K$_2$PtCl$_4$ (415 mg, 1 mmol) was dissolved in 50 mL of DDW to which (1.330 gr, 8 mmol) KI were added and the red solution was stirred at r.t. for 20 minutes. To the stirred solution (202 µl, 2 mmol) of piperidine were added slowly. After 1 hr of stirring at r.t. the yellow precipitate was collected and washed with 50 mL of DDW and then with 50 mL of ether. Cis-[PtI$_2$(Pip)$_2$] (300 mgs, 0.484 mmol) was taken up in 20 mL DMF and, 164.5 mgs (0.97 mmol) of AgNO$_3$ and (98 µl, 1.94 mmol) were added and the mixture was stirred overnight at r.t. After filtering off the precipitate the solution was evaporated to dryness. To the gum 20 mL of DDW were added and stirred for 30 minutes. The non-soluble materials were filtered and 2 mL of concentrated HCl were added. The acidified solution was wormed to 90° C. for 5 hrs. After cooling to r.t. the yellow precipitate was collected and washed with 50 mL DDW and 40 mL ether.

Trans-[PtCl$_2$(piperidine)$_2$] (6): Yield: 91%. Anal. (C$_{10}$H$_{22}$Cl$_2$N$_2$Pt): C,H,N. $^{195}$Pt NMR($\delta$, DMF): −2080 ppm.

Procedure for Preparing cis-[PtCl$_2$(NH$_3$)(piperidine)] (7)

K$_2$PtCl$_4$ (415 mg, 1 mmol) of was dissolved in 50 mL of DDW, and 8 eq. KI (1.328 g, 8 mmol) were added. The mixture was stirred at r.t. for 15 min., and then 2 eq. of piperidine (198 µL, 2 mmol) were added slowly. The mixture was stirred for 1 h at r.t., during which a yellow precipitate was formed. The precipitate was collected and washed thoroughly with 50 mL of DDW, and with 20 mL of a (1:1) acetone: diethyl ether mixture. After drying, the yellow precipitate (500 mg, 0.8 mmol) was suspended in a mixture of 20 mL of DDW and 40 mL of ethanol, to which 1 mL of perchloric acid (70%) was added. The suspension was stirred at r.t. for 8 days. During this period, the yellow precipitate turned to brown. The brown precipitate was collected by filtration and washed with 40 mL of DDW and 20 mL of acetone:diethylether (1:1). After drying, the precipitate was re-suspended in 20 mL of DDW, 0.5 mL of 25% NH$_4$OH was added dropwise, and the mixture was vigorously stirred for 24 h, during which the brown-colored precipitate turned to yellow. The yellow precipitate was collected and washed thoroughly with 50 mL of DDW, and 10 mL of acetone-diethyl ether and dried by continuous suction. The product was characterized as the mixed cis-amine-piperidine-diiodoplatinum(II) [$^{195}$Pt NMR($\delta$, DMF)= −3260 ppm].

Cis-amine-piperidine-diiodoplatinum(II) (300 mg, 0.54 mmol) was suspended in 20 mL DDW, and 2 eq of AgNO$_3$ (184.9 mg, 1.08 mmol) were added. The suspension was vigorously stirred in the dark for 24 h. The AgI precipitate was filtered off, and the aqueous filtrate was transferred into a 50-mL vessel, to which 0.5 g of KCl were added. The colorless solution turned yellowish, and the dichloro-diamineplatinum(II) product started precipitating. After 4 h at r.t. the yellowish precipitate (260 mg) was collected and washed thoroughly with 50 mL of DDW and dried by washing with 100 mL of diethyl ether.

Overall yield of cis-[PtCl$_2$(NH$_3$)(piperidine)] (7): 69%. Anal. (C$_5$H$_{14}$Cl$_2$N$_2$Pt) C,H,N. $^{195}$Pt NMR($\delta$, DMF): −2159 ppm.

(2) Synthesis of Pt Piperazine Complexes

One aim of the research presented herein was to design and prepare platinum complexes that are water-soluble, react rapidly with DNA and are able to form adducts with DNA that are different from those formed by cisplatin and transplatin. This led to the design and synthesis of several additional trans-Pt derivatives with the piperazine as a ligand. This ligand was chosen since it would confer positive charge to the complex and thus would ensure adequate aqueous solubility and rapid interaction with the polyanionic DNA; it is a non-planar heterocyclic amine ligand that is flexible and has a hydrogen bond donor that can interact with the DNA to form a lesion; and it is bulky enough to affect kinetics and cytotoxicity.

Trans-[PtCl$_2$(NH$_3$)(piperazine)].HCl (8)

Cis-diammine-dichloroplatinum(II), (300 mg, 1 mmol) was dissolved in 30 mL of DMF and 2 eq. (372.52 mg, 2 mmol) of tert-butyl 1-piperazine carboxylate and 2 eq. (339.76 mg, 2 mmol) of AgNO$_3$ were added simultaneously with stirring. Stirring continued in the dark for 24 h at room temperature. The precipitate was filtered off through a celite sinter glass and the filtrate was evaporated to dryness under reduced pressure. The resulting gum was dissolved in 30 mL of DDW and 2 mL of concentrated HCl were added and the reaction mixture was stirred at r.t. for 24 h. The colored precipitates were removed and the solution was heated to 85–90° C. for 60 min. After cooling to room temperature the reaction mixture was filtered and the filtrate was chilled to 0° C. for 72 h. The yellow precipitate was filtered and washed with 10 mL of ice-cold DDW and 30 mL of diethyl ether. After drying, the yellow product (300 mg) was characterized as the hydrochloride salt of the desired trans-ammine-piperazine-dichloroplatinum(II) (8)

Trans-[PtCl$_2$(NH$_3$)(piperazine)].HCl (8) Yield: 74%. Anal. Calcd. for C$_4$H$_{14}$Cl$_3$N$_3$Pt.H$_2$O: C, 11.34%; H, 3.81%; N, 9.92%. Found: C, 11.27%; H, 3.56%; N, 9.86%. $^{195}$Pt-NMR($\delta$, H$_2$O): −2177 ppm.

General Procedure for Preparing trans-[PtCl$_2$(Am1)(piperazine)].HCl

In the following description Am1 refers to any one of the following amines: n-butyl amine, isopropyl amine, 4-picoline, piperidine, piperazine.

Synthesis of the intermediate cis-[PtI$_2$(tert-butyl 1-piperazine carboxylate)$_2$]: Potassium tetrachloroplatinate (1 g, 2.4 mmol) was dissolved in 40 mL of DDW and 8 eq. (3.2 g, 19.27 mmol) of KI were added. The mixture was stirred at r.t. for 15 min. Two eq. (0.9 g, 4.8 mmol) tert-butyl 1-piperazine carboxylate were added and the mixture was vigorously stirred for 1 h at r.t. Throughout this period of time the desired diiododiamineplatinum(II) precipitated. The yellow precipitate was collected by filtration, washed with 50 mL of DDW and dried by suction.

Cis-[PtI$_2$(tert-butyl 1-piperazine carboxylate)$_2$]: Yield: 89%, $^{195}$Pt-NMR($\delta$, DMF): −3264 ppm.

Cis-[PtI$_2$(tert-butyl 1-piperazine carboxylate)$_2$ (411 mg, 0.5 mmol) was dissolved in the dark in 15 mL of DMF and 2 equiv (169.88 mg, 1 mmol) of AgNO$_3$ were added simultaneously with 2 eq. of the corresponding amine (98.83 μL of n-butylamine, 85.17 μL of isopropylamine, 97.4 μL of 4-picoline, 99 μL of piperidine, or 186 mg tert-butyl 1-piperazine carboxylate). Stirring continued in the dark for 24 h at r.t. The precipitate was flittered off through a celite sinter glass. The filtrate was evaporated to dryness under reduced pressure. The resulting gum was dissolved in 30 mL of DDW and 2 mL of concentrated hydrochloric acid were added and the reaction mixture was stirred at room temperature for 24 h. The colored precipitates were removed and the solution was heated to 85–90° C. for 60 min. After cooling to room temperature the reaction mixture was filtrated and the filtrate was chilled to 0° C. for 24 hours. The yellow precipitate was filtered and washed with 20 mL of ice cooled DDW and 30 mL of diethyether. After drying, the yellow products were characterized as the hydrochloride salts of the desired trans-diamine-dichloroplatinum(II) complex.

Trans-[PtCl$_2$(isopropylamine)(piperazine)].HCl (9): Yield 71%, $^{195}$Pt-NMR($\delta$, H$_2$O): −2226 ppm.

Trans-[PtCl$_2$(n-butylamine)(piperazine)].HCl (10): Yield 67%, $^{195}$Pt-NMR($\delta$, H$_2$O): −2221 ppm.

Trans-[PtCl$_2$(n-nonylamine)(piperazine)].HCl (11): Yield 77%, $^{195}$Pt-NMR($\delta$, H$_2$O): −2236 ppm.

25.06%, H: 3.82%, N: 8.55%, $^{195}$Pt-NMR($\delta$, H$_2$O): −2086 ppm.

Trans-[PtCl$_2$(piperidine)(piperazine)].HCl (12): Yield 56%, $^{195}$Pt-NMR($\delta$, H$_2$O): −2230 ppm.

Trans-[PtCl$_2$(4-picoline)(piperazine)].HCl (13): Yield 61.2%, Anal. Calc. For C$_{10}$H$_{18}$Cl$_3$N$_3$Pt: C: 24.99%, H: 3.56%, N: 8.74%, Found: C: 25.06%, H: 3.82%, N: 8.55%, Trans-[PtCl$_2$(piperazine)(piperazine)].HCl (14): Yield 83%, $^{195}$Pt-NMR($\delta$, H$_2$O): −2238 ppm.

Trans-[PtCl$_2$(NH$_3$)[4-(2-hydroxyethyl)piperazine)].HCl (15): Yield 83%, $^{195}$Pt-NMR($\delta$, H$_2$O): −2238 ppm.

Procedure for the Preparation of cis-[PtCl$_2$(NH$_3$)(piperazine)].HCl (16)

Tetraphenylphosphonium trichloro-monoammine-platinum(II) (300 mg, 0.45 mmol) were dissolved in 10 mL of 1:1 acetone/DDW mixture. To the orange-colored solution 1 equiv (77.53 mg, 0.45 mmol) tert-butyl 1-piperazine carboxylate was added. The mixture stirred in a closed vessel at r.t. for 7 days. After evaporating the solution to dryness under reduced pressure the yellow solid was taken in 10 mL of absolute ethanol and 0.5 mL of concentrated hydrochloric acid was added and the mixture was allowed to stand for overnight. The yellow precipitate was collected by filtration and washed with 10 mL of ethanol.

Cis-[PtCl$_2$(NH$_3$)(piperazine)].HCl: Yield: 58%, $^{195}$Pt-NMR($\delta$, H$_2$O): −2187 ppm.

EXAMPLE 2

Biological Assays

Cell Cultures

A human ovarian carcinoma cell line (OV-1063), established at the Hadassah University hospital and human colon carcinoma cell line (C-26) were maintained in RPMI-1640 medium supplemented with 10% FCS, antibiotics and glutamine. All culture medium components were purchased from Biological Industries (Beit-HaEmek, Israel). Both cell lines were maintained at 37° C. in a water-jacketed CO$_2$ incubator.

Further, three pairs of cisplatin sensitive and resistant cancer cell lines (A2780/A2780cisR, 41M$_r$/41McisR and CH1/CH1cisR) were employed[15]. These pairs of cell lines were selected on the basis of encompassing all of the known major mechanisms of resistance to cisplatin: 41McisR being resistant primarily through reduced drug transport[16], CH1cisR through enhanced DNA repair/tolerance[17] and A27780cisR through a combination of decreased uptake, enhanced DNA repair/tolerance and elevated GSH levels[18].

Drugs

Cisplatin and transplatin were supplied by (Sigma, St Louis, Mo., USA). All drugs were dissolved in normal saline immediately before the experiments.

Methylene Blue Assay of Cell Survival

Cytotoxicity of the synthesized complexes was tested by the methylene blue (MB) staining assay[19]. A fixed number of exponentially growing cells in 200 μl medium were plated in 96-microwell, flat-bottomed plates. For each of the complexes tested, 4 well were used. Following 24 hr in culture, 20 μl of different concentration of the complexes were added to each well containing untreated cells. Normal saline was added to the controls. Cells were exposed to complexes for 4, 24, or 72 hr. At the end of exposure for a fixed time interval, the treated cells as well as parallel control cells were washed and incubation was continued in fresh medium until termination of the experiment. Following 72 hr of growth, cells were fixed by adding 50 μl of 2.5% of glutaraldehyde to each well for 15 min. Fixed cells were rinsed 10 times with fresh de-ionized water and once with borate buffer (0.1 M, pH=8.5), dried and stained with MB (100 μl of 1% solution in 0.1 M borate buffer, pH=8.5) for 1 hr at room temperature. Stained cells were rinsed thoroughly with de-ionized water to remove any non-cell-bound die and then dried. The MB bound to the fixed cells was extracted by incubation at 37° C. with 200 μl of 0.1N HCl for 1 hr, and the net optical density (OD) of the die in each well was determined by a plate spectrophotometer (Labsystems Multyskan BICHROMATIC, Finland) at 620 nm.

The advantage of the MB method with 96-microwell plates is the possibility of running a wide range of experiments on the rate of cell proliferation and survival with a large number of data points, where cells are grown in the same plate and assayed exactly in the same conditions for different experimental complexes. The validity of the MB assay for evaluating cell survival is supported by the high correlation between the MB colorimetric assay and colony-forming units assay results[20].

Microculture Tetrazolium (MTS) Assay and Cell Survival

Cytotoxicity of the synthesized complexes was also tested by the MTS method[21]. Accordingly, the compounds were incubated for 24 hours with the corresponding cell lines and the cell survival in compound-treated cultures was evaluated.

Platinum Complex Intracellular Accumulation Measurement

Cells were seeded for 48 hr before one of the complexes was added to the culture medium. After 24 hr of exposure, the complexes were removed and the cells washed twice with ice-cold PBS and pelleted. The cells ($1*10^6$) were dried and mineralized by heating for 10 min in 65% $HNO_3$ (BDH, England)[22]. Samples were dissolved in de-ionized water and each sample was measured at two different dilutions by flameless Zeeman atomic absorption spectrometer (FAAS). The calibration curves included 5 standards of $K_2PtCl_4$ stock solution with concentrations ranging from 50 to 250 ng platinum per ml. Platinum content was expressed as picomoles platinum per $1*10^6$ cells.

Determination of Pt-DNA Adducts by FAAS

Cells were seeded for 48 hr before one of the drugs was added to the culture medium. After 24 hr of exposure, the complexes were removed and the cells washed twice with ice-cold PBS and pelleted. DNA from platinum-containing material ($2*10^6$ cells) was extracted from the cell pellet by QIAamp DNA Blood Kit (QIAGEN, Germany) according to the manufacture instructions. DNA yield was determined by measuring the concentration of DNA in the eluate by absorbance at 260 nm. The DNA isolated from each sample averaged 50±10 μg/ml. Purity is determined by calculating the ratio of absorbance at 260 nm to 280 nm; the grade of purification of DNA was on average 95%.

Determination of Pt-DNA Adducts by EtBr Fluorescence

A plasmid (4.8 kbp) containing a gene coding for human growth hormone, plasmid pS16-hGH, was prepared as previously described[23]. The freshly prepared DNA was analyzed by agarose gel (1%) electrophoresis using post-staining with SYBR Green I fluorescent dye (Molecular Probes, Eugene, Oreg.). Quantitative analysis of supercoiled plasmid[24] was performed and showed that the plasmid DNA was 85–90% in a supercoiled form. UV-spectroscopy showed no presence of protein or RNA contamination in any of the DNA batches. The ratio of absorbance at 260 nm to that at 280 nm was always between 1.8 and 1.9.

DNA were modified by the platinum complexes in 10 mM $NaClO_4$ (pH 7.0) at 37° C. in the dark for 24 hr. Measurements of EtBr fluorescence were performed on an LS50B luminescence spectrometer (Perkin Elmer, Norwalk, Conn.). Fluorescence measurements of DNA modified by platinum in the presence of EtBr were performed using the excitation wavelength of 546 nm (slit 10 run) and emission wavelength of 590 nm (slit 10 nm) at 25° C. The concentrations were 0.01 mg/ml for DNA and 0.04 mg/ml for EtBr, which corresponded to the saturation of all intercalation sites of EtBr in DNA.

Assessment of Apoptosis

Apoptosis was assessed by two approaches:

(1) By staining of the C-26 and OV-1063 cells with Merocyanine 540 (MC 540) (Molecular probes, Oregon, USA) and 4', 6-diamidino-2-phenylindone dihydrochloride (DAPI) (Molecular probes, Oregon, USA). This assay is based on the observation that soon after the initiation of apoptosis, phosphatidylserine (PS) translocates from the inner face of the plasma membrane to the cell surface. At this point, PS can be easily detected by staining with MC 540, which has a strong affinity to PS[25]. Chromatin condensation was assessed by staining with DAPI, which preferentially stains double stranded DNA. In the following experiments samples containing $5*10^5$ cells were cultured on 6-well plates covered with a glass coverslip. After treatment of cells with $IC_{50}$ of the complexes, cells were washed with PBS and incubated for 2 min in the dark in 500 μl of PBS containing 2.5 μl of MC 540 (1 mg/ml). After that cells were washed with PBS, fixated with 4% formaldehyde and stained with 300 μl DAPI (3 μM). Thereafter, glass coverslip was placed on a glass slide and photographed using a fluorescence confocal microscope.

(2) By the EnzChektm Caspase-3 Assay Kit (Molecular probes, Eugene, Oreg.). This Kit allows the detection of apoptosis by assaying for increases in caspase-3 and other DEVD-specific protease activities (e.g., caspase-7). The basis for the assay is rodamine 110 bis-(N-CBZ-aspartil-L- glutarnyl-L-valyl-aspartic acid amide) (Z-DEVD-R110). This substrate is a bisamide derivative of rhodamine 110 (R110) containing DEVD peptides covalently linked to each of R110's amino groups. Upon enzymatic cleavage, the non-fluorescent bisamide substrate converted to the fluorescent R110, which can be quantified by fluorescence microplate reader using excitation at 485±10 nm and emission detection at 535±10 nm.

Briefly, C-26 and OV-1063 cells were treated with IC50 of trans-[PtCl$_2$(4-picoline)(piperidine)] (5) (4.5 μM and 6.5 μM, respectively) and of trans-[PtCl$_2$(4-picoline)(piperazine).HCl] (12) (5 μM and 7.5 μM, respectively) for 5 or 16 hr. Both "induced" and "control" cells were then harvested and lysed. Enzyme reactions were performed in 96-well plates with 50 μg of cytosolic proteins (55 minutes of incubation) and with a final concentration of 25 μM Z-DEVD-R110 substrate as described in the kit protocol.

positively charged complexes of the general formula [PtCl$_2$(Am)(pz)].HCl. The Compounds presented herein were shown to be more soluble than their neutral counterparts having solubilities in the range of 20 mM compared with 6.3 mM for cisplatin and 0.8 mM for transplatin. For example, trans-[PtCl$_2$(4-picoline)(piperazine)].HCl (13) exhibited solubility in DDW (at 37° C.) 7.5 mg/ml (18.0 mM).

Biological Activity

In Vitro Growth Inhibition

In order to assess the anti-tumor activity of the synthesized trans and cis complexes C-26 and OV-1063 cells were incubated for 4, 24, or 72 hrs with these complexes. MB cytotoxicity assay revealed that replacing one (NH$_3$) or both of the transplatin enhances significantly (by more than fourfold) the cytotoxicity of the new trans-PtCl$_2$ compounds in both C-26 and OV-1063 cancer cell lines (Table 1).

TABLE 1

IC$_{50}$ of complexes against C-26 cells and OV-1063 cells as compared to cisplatin and transplatin

| | | C-26 cells | | | OV-1063 cells | | |
|---|---|---|---|---|---|---|---|
| | Complex No. | IC$_{50}$, μM 4 h | IC$_{50}$, μM 24 h | IC$_{50}$, μM 72 h | IC$_{50}$, μM 4 h | IC$_{50}$, μM 24 h | IC$_{50}$, μM 72 h |
| Cisplatin | | 1.5 ± 1.3 | 0.6 ± 0.1 | 0.2 ± 0.2 | 2.0 ± 0.5 | 0.7 ± 0.2 | 0.5 ± 0.2 |
| Transplatin | | 64.0 ± 2.0 | 46.0 ± 3.1 | 41.0 ± 1.7 | 81.0 ± 4.3 | 73.0 ± 5.1 | 52.0 ± 3.2 |
| trans-[PtCl$_2$(4-picoline)(piperidine)] | 5 | 4.5 ± 0.7 | 2.5 ± 0.7 | 1.75 ± 1.0 | 6.5 ± 0.7 | 6.0 ± 1.4 | 4.5 ± 2.1 |
| trans-[PtCl$_2$(NH$_3$)(4-picoline)] | | 12.0 ± 1.2 | 11.0 ± 2.0 | 11.0 ± 1.1 | 18.0 ± 3.7 | 16.0 ± 3.5 | 14.0 ± 2.3 |
| trans-[PtCl$_2$(NH$_3$)(piperidine)] | 1 | 8.5 ± 2.0 | 7.7 ± 2.0 | 7.0 ± 2.5 | 11.0 ± 2.0 | 9.5 ± 1.7 | 8.7 ± 1.4 |
| trans-[PtCl$_2$(4-picoline)(piperazine)].HCl | 13 | 5.5 ± 1.0 | 4.5 ± 0.75 | 3.5 ± 0.8 | 7.4 ± 1.5 | 6.0 ± 1.0 | 5.1 ± 0.9 |
| cis-[PtCl$_2$(NH$_3$)(4-picoline)] | | 5.1 ± 1.2 | 4.7 ± 2.4 | 3.7 ± 1.6 | 6.0 ± 2.2 | 5.1 ± 1.9 | 4.0 ± 1.7 |
| cis-[PtCl$_2$(NH$_3$)(piperidine)] | 7 | 2.6 ± 1.7 | 2.1 ± 1.2 | 1.3 ± 0.7 | 4.2 ± 1.7 | 3.1 ± 1.2 | 2.6 ± 0.7 |
| trans-[PtCl$_2$(NH$_3$)].HCl (4-piperidino-piperidine) | 3 | 2 | 0.7 | 0.4 | 4.5 | 1.7 | 0.9 |
| cis-[PtCl$_2$(NH$_3$)(piperazine)].HCl | 15 | >10 | >10 | 5 | NA | NA | NA |

$^a$IC$_{50}$ in μM, mean ± SD from at least 2 experiments.

In Vivo Toxicity and Anti-tumor Effect

The trans-platinum(II) derivates, trans-[PtCl$_2$(NH$_3$)(4-piperidino-piperidine)] (3) was evaluated for its toxicity and antitumor efficacy as compared to cis-DDP.

Toxicity

Toxicity of the trans-[PtCl$_2$(NH$_3$)(4-piperidino-piperidine)] was evaluated on 8 week-old female BALB/C mice and compared to cis-DDP. This novel complex and cis-DDP at different concentrations were injected i.v., three times at weekly intervals, and animal weight and survival were evaluated.

Antitumor Efficacy

Female BALB/C mice (in the weight range of 17–20 g) were injected i.p. with 1*10$^6$ C-26 colon carcinomas. The viability of these cells was >90% by trypan blue exclusion.

The therapeutic efficacy of trans-[PtCl$_2$ (NH$_3$)(piperidino-piperidine)].HCl (3) was studied and compared to cis-DDP. Treatment began at day 3 after tumor inoculation and was repeated twice for a total of three injections at weekly intervals.

Results

Solubility of the Pt Complexes

The low solubility of the neutral diaminedichloro platinum(II) compounds, that results in poor bioavailability, was one of the reasons for the design and synthesis of the Replacement of one NH$_3$ group by either an aromatic-planar amine (4-picoline) to give trans-[PtCl$_2$(NH$_3$)(4-picoline)]or by an aliphatic non-planar amine (piperidine) to give trans-[PtCl$_2$(NH$_3$)(piperidine)] (1) enhanced the cytotoxic activity relative to transplatin (Table 1). It should be noted that complex (1) was more cytotoxic than the [trans-[PtCl$_2$(NH$_3$)(4-picoline)] derivate which suggests that activation of the trans position can be achieved by sterically hindered amine ligands. Piperidine is more sterically hindered than the 4-picoline because of the hydrogen atoms pointing out in opposite directions in contrast to the planar hydrogens of the aromatic ring of 4-picoline which may correlate with cytotoxic activity.

Figure 1B:
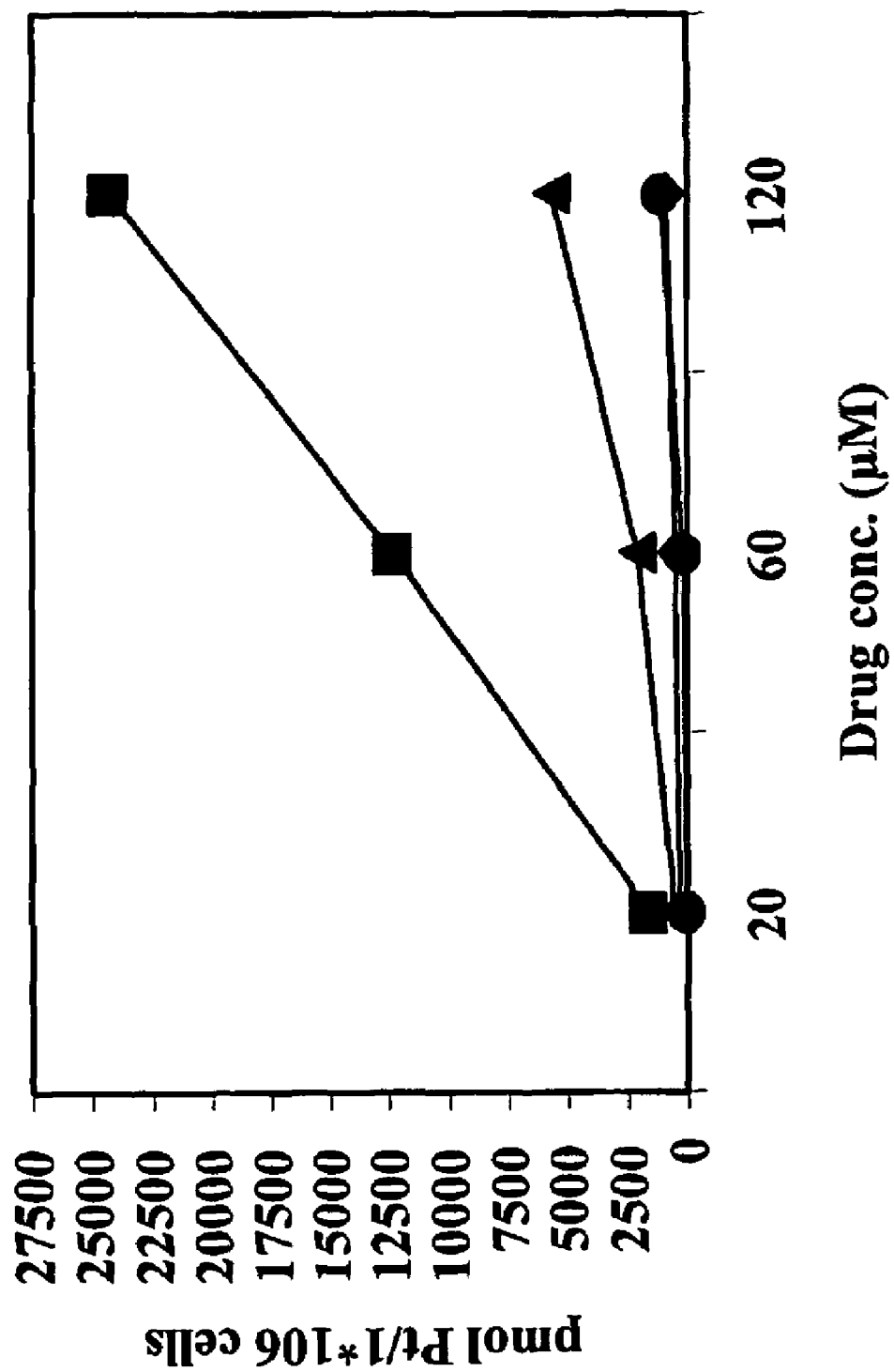

In addition, replacing the second NH$_3$ in trans-[PtCl$_2$ (NH$_3$)(4-picoline)] with piperidine to give the mixed trans-[PtCl$_2$(4-picoline)(piperidine)] (5) enhanced the compound's cytotoxicity by a factor of 2–3 (Table 1). This observation may be explained by a higher sterically hindered structure of complex (5). The trans-[PtCl$_2$(4-picoline)(piperidine)] was 3 folds less active than cisplatin and the is higher IC$_{50}$ values of trans-[PtCl$_2$(4-picoline)(piperidine)] were consistent with the lower level of Pt-DNA adducts as shown in FIGS. 1A and 1B.

The cytotoxicity of the sterically hindered compounds of the trans geometry was compared with that of their cis counterparts cis-[PtCl$_2$(NH$_3$)(4-picoline)] and cis-[PtCl$_2$(NH$_3$)(piperidine)] (7). In contrast with the effect of replacing one $NH_3$ in the new trans-Pt complexes, a similar replacement of one $NH_3$ of cisplatin by an aromatic-planar amine ligand (4-picoline) or by an aliphatic non-planar amine (piperidine) resulted in lower cytotoxic activity as compared to cisplatin itself. The complex cis-[PtCl$_2$(NH$_3$)(piperidine)] is an analogue to the new active cis-[Pt(NH$_3$)(2-picoline)] (AMD473) a novel sterically hindered anti-tumor compound designed to circumvent platinum drug resistance and is currently under clinical trials[26].

The cytotoxicity of several of the piperazine-containing Pt complexes on cisplatin sensitive and resistance cancer cell lines was also determined. In particular, three pairs of cisplatin sensitive and resistant cancer cell lines (A2780/A2780cisR, 41M/41McisR and CH1/CH1cisR) were employed.

The complexes were incubated for 24 hours with the above mentioned cell lines and the cell survival in compound-treated cultures was evaluated by the (microculture tetrazolium) MTS method as previously reported. The results of the IC$_{50}$ studies are shown in Table 2A–2B.

resistant through enhanced DNA repair/tolerance and elevated GSH levels. Especially noticeable are the very low resistance factors (RF) of trans-[PtCl$_2$(NBA)(pz)].HCl (10) against all three cell lines (RF<2) indicating efficient circumvention of cisplatin resistance.

A possible explanation for the enhancement of anti-tumor activity of these transplatin complexes is that the sterically hindered ligands may decrease detoxification by thiols. The reduced reactivity towards biological thiols and thioethers (proteins and peptides) is considered beneficial since reaction of cisplatin with biological sulfur containing ligands is believed to be in the source of acquired resistance and the toxic side effects of the drug.

Cellular Drug Uptake and DNA Platination

In order to determine drug accumulation in tumor cells, C-26 and OV-1063 cells were exposed to the cytotoxic compounds trans-[PtCl$_2$(4-picoline)(piperidine)] (5) and trans-[PtCl$_2$(4-picoline)(piperazine).HCl] (13) for 24 hr and compared with the drug uptake of cisplatin and transplatin

TABLE 2A

IC$_{50}$ mean values (μM) obtained for several piperidine (pip) containing complexes (the number in brackets represents resistance factor)

|  | A2780 | A2780 cisR | CH1 | CH1cisR | 41M | 41McisR |
|---|---|---|---|---|---|---|
| trans-PtCl$_2$(4-pic)(pip) | 9 ± 1 | 135 ± 7 (15) | 26 ± 3 | 169 ± 9 (6.5) | 35 ± 4 | 210 ± (6.0) |
| trans-PtCl$_2$(NH$_3$)(4-pip)Cl$_2$ | 5 ± 0.7 | 20 ± 2 (4.0) | 15 ± 2 | 94 ± 6 (6.3) | 27 ± 2 | 150 ± 8 (5.5) |
| trans-PtCl$_2$(pip)$_2$ | 15 ± 2 | 250 ± 12 (16.7) | 35 ± 2 | 280 ± 12 (8) | 50 ± 3 | 300 ± 25 (6) |
| cis-PtCl$_2$(pip)$_2$ | 15 ± 2 | 250 ± 12 (16.7) | 32 ± 2 | 280 ± 12 (8) | 50 ± 3 | 300 ± 25 (6) |
| cis-PtCl$_2$(NH$_3$)(pip) | 26 ± 3 | 234 ± 17 (9) | 36 ± 4 | 263 ± 17 (7.3) | 64 ± 5 | 315 ± 24 (4.9) |
| Transplatin | >200 | >200 | >200 | >200 | >200 | >200 |
| Cisplatin | 2.2 | 38 | 6 | 23 | 26 | 107 |

TABLE 2B

IC$_{50}$ mean values (μM) obtained for several piperazine-(pz) containing complexes

|  | A2780 | A2780cisR | CH1 | CH1cisR | 41M | 41McisR |
|---|---|---|---|---|---|---|
| trans-[PtCl$_2$(NH$_3$)(pz)].HCl | 5 ± 1 | 44 ± 4 (8.8) | 12 ± 3 | 34 ± 4 (2.8) | 52 ± 5 | 155 ± 12 (3.0) |
| trans-[PtCl$_2$(NBA)(pz)].HCl | 16 ± 2 | 28 ± 2 (1.8) | 17 ± 2 | 19 ± 3 (1.1) | 32 ± 5 | 48 ± 3 (1.5) |
| trans-[PtCl$_2$(IPA)(pz)].HCl | 14 ± 1 | 30 ± 2 (2.1) | 10 ± 1 | 50 ± 3 (5.0) | 38 ± 3 | 122 ± 8 (3.2) |
| trans-[PtCl$_2$(4-pic)(pz)].HCl | 10 ± 3 | 24 ± 3 (2.4) | 16 ± 2 | 42 ± 3 (2.6) | 45 ± 3 | 147 ± 10 (3.3) |
| trans-[PtCl$_2$(pip)(pz)].HCl | 18 ± 2 | 64 ± 5 (3.6) | 22 ± 3 | 85 ± 7 (3.9) | 37 ± 4 | 118 ± 9 (3.2) |
| trans-[PtCl$_2$(pz)(pz)].HCl | 17 ± 3 | 43 ± 3 (2.5) | 26 ± 2 | 53 ± 3 (2.0) | 43 ± 3 | 153 ± 10 (3.6) |
| cis-[PtCl$_2$(NH$_3$)(pz)].HCl | 10 ± 1 | 25 ± 2 (2.5) | 28 ± 2 | 56 ± 3 (2.0) | 46 ± 3 | 112 ± 12 (2.4) |
| trans-PtCl$_2$(NH$_3$)$_2$ | >200 | >200 | >200 | >200 | >200 | >200 |
| cis-PtCl$_2$(NH$_3$)$_2$ | 2.2 ± 0.6 | 38 ± 3 (17.3) | 6 ± 1 | 23 ± 3 (3.8) | 26 ± 2 | 107 ± 8 (4.1) |

NBA = n-butylamine,
IPA = isopropylamine,
4-pic = 4-methylpyridine,
pip = piperidine,
pip-piperazine.
The numbers in parentheses are the resistance factors (IC$_{50}$ resistant/IC$_{50}$ sensitive)

In terms of the SAR, replacing one or both amine ligands of transplatin with piperazine markedly increases the anti-tumor activity relative to transplatin indicating the positively charged non-planar amine ligand (piperazine) can activate the trans geometry. The most striking feature of these cytotoxicity studies is that the complexes are at least as active as cisplatin against the A2780cisR cell line that is under the identical conditions. The Pt content associated with the cells was measured by Atomic Absorption Spectroscopy (AAS). It was found that trans-[PtCl$_2$(4-picoline)(piperidine)] (5) penetrates the cells very efficiently in both cell lines (6-fold higher than cisplatin), as shown in FIG. 1A.

Also, compared to transplatin the penetration of trans-[PtCl$_2$(4-picoline)(piperidine)] (5) was 7-fold higher in OV-1063 cells and 30-fold higher in C-26 cells, as shown in FIG. 1B). A time-dependent increase of trans-[PtCl$_2$(4-picoline)(piperidine)] (5) accumulation was observed during the 4 (data not shown) to 24 hr of drug exposure. The time-dependent accumulation of Pt in the cells was consistent with the decrease in the IC$_{50}$ values (Table 1). The trans-[PtCl$_2$(4-picoline)(piperazine)].HCl (13) showed the highest penetration values in both cell lines (22-fold higher in compartment to cisplatin) (FIGS. 1A and 1B).

Figure 2A:
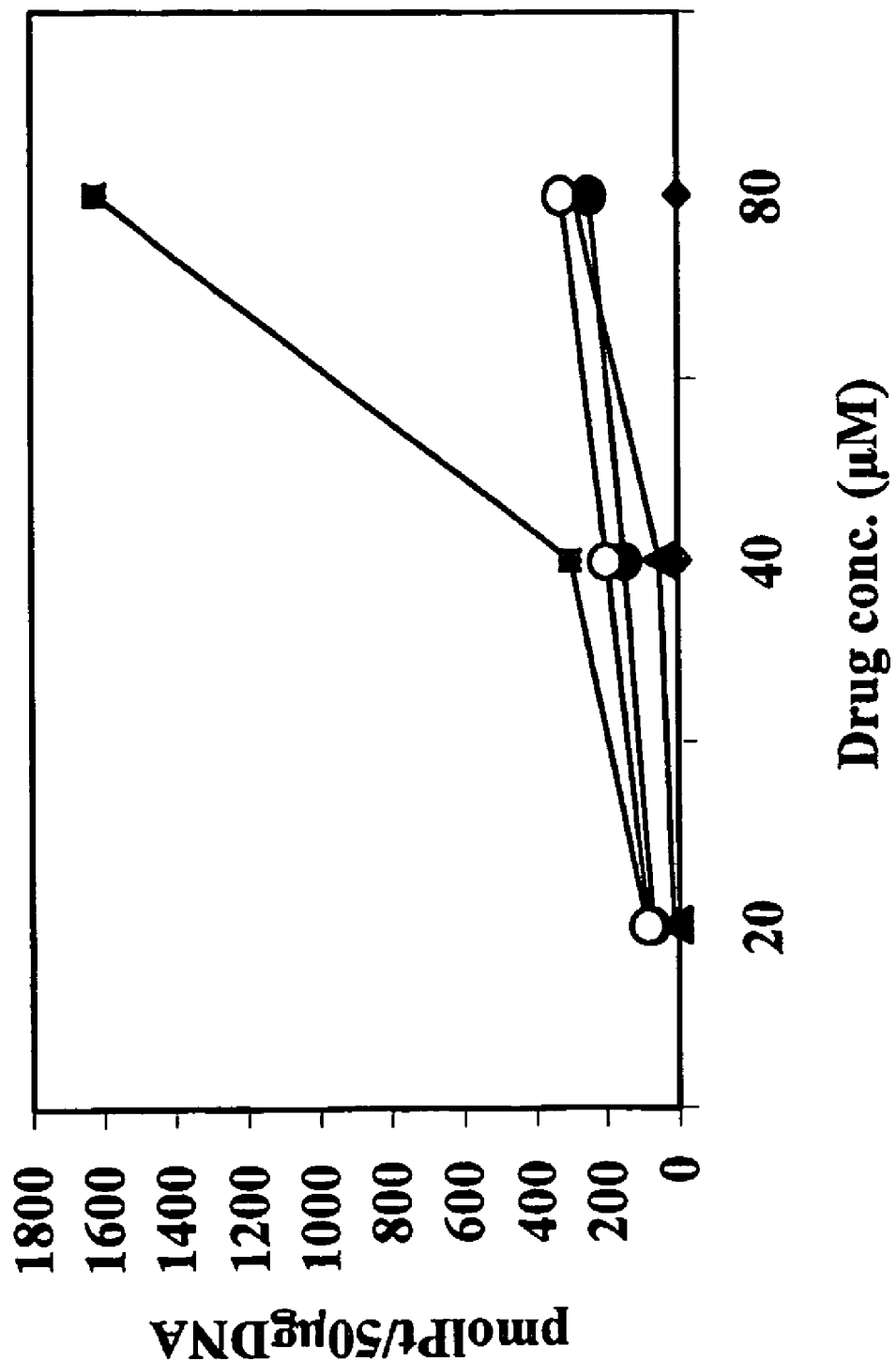
FIGS. 2A–2B show DNA platination levels in C-26 cancer cells (FIG. 2A) or OV-1063 cancer cells (FIG. 2B) of cisplatin (-?-); transplatin (-|-); trans-[PtCl$_2$)(4-picoline)(piperidine)](-^-);trans-[PtCl$_2$)(4-picoline)(piperazine)].HCl (-|-) and trans-[PtCl$_2$(NH$_3$)(piperidino-piperidine)].HCl (-o-). The Pt content was determined by Atomic Absorption Spectroscopy (AAS).
Figure 2B:
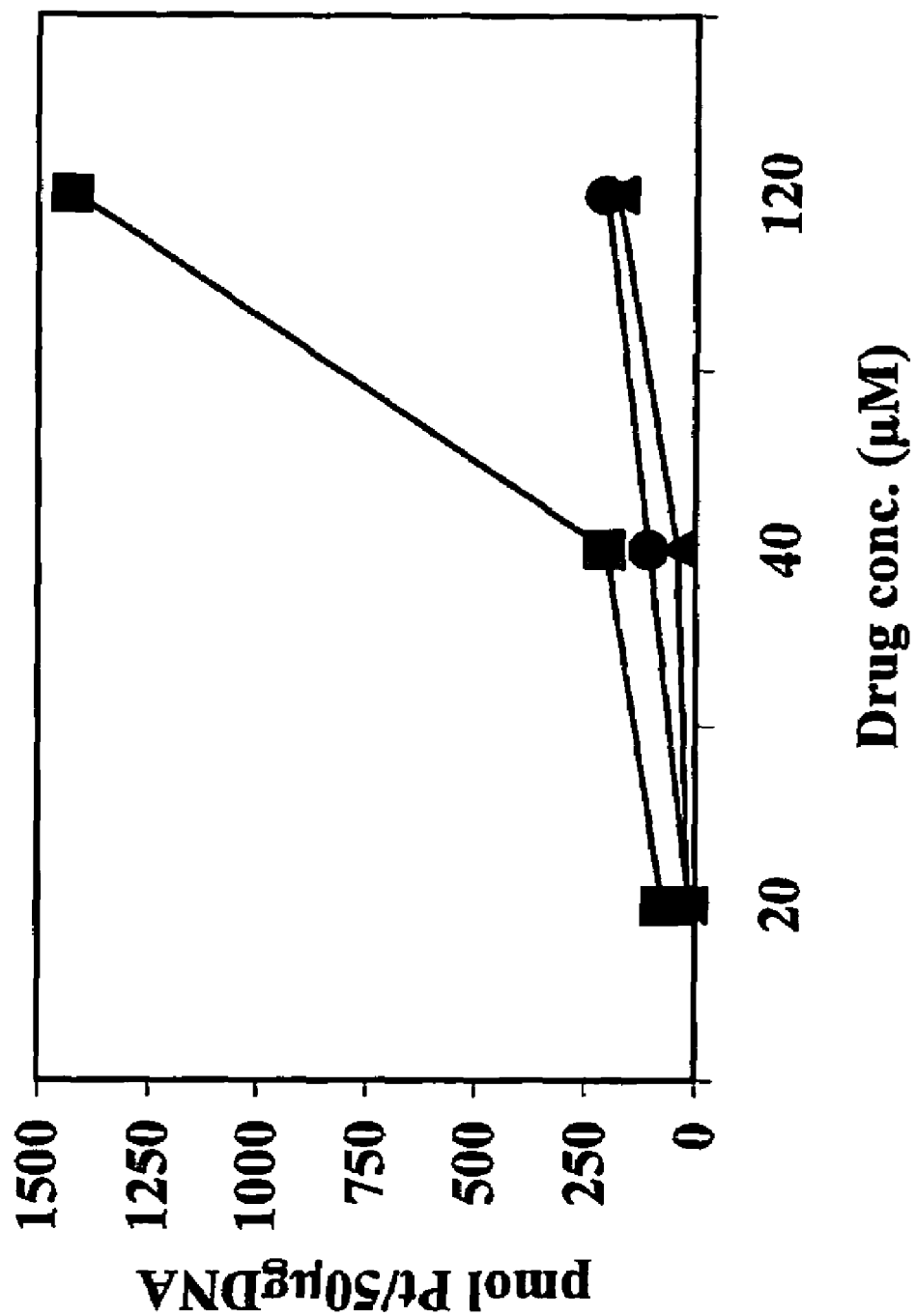

To determine the cellular DNA platination, C-26 cells and OV-1063 cells were exposed to these transplatin complexes for 4 hr or 24 hr and compared with cisplatin and the platinum DNA content was measured by AA spectrometer. The trans-[PtCl$_2$(4-picoline)(piperidine)] DNA platination was the same as that of Cis-Pt in C-26 and OV-1063 cells and the values of Pt molecules intercalated with DNA from trans-[PtCl$_2$(4-picoline)(piperazine)].HCl complex were 7-fold higher than of Cis-Pt in both cell lines (FIGS. 2A and 2B).

Figure 3:
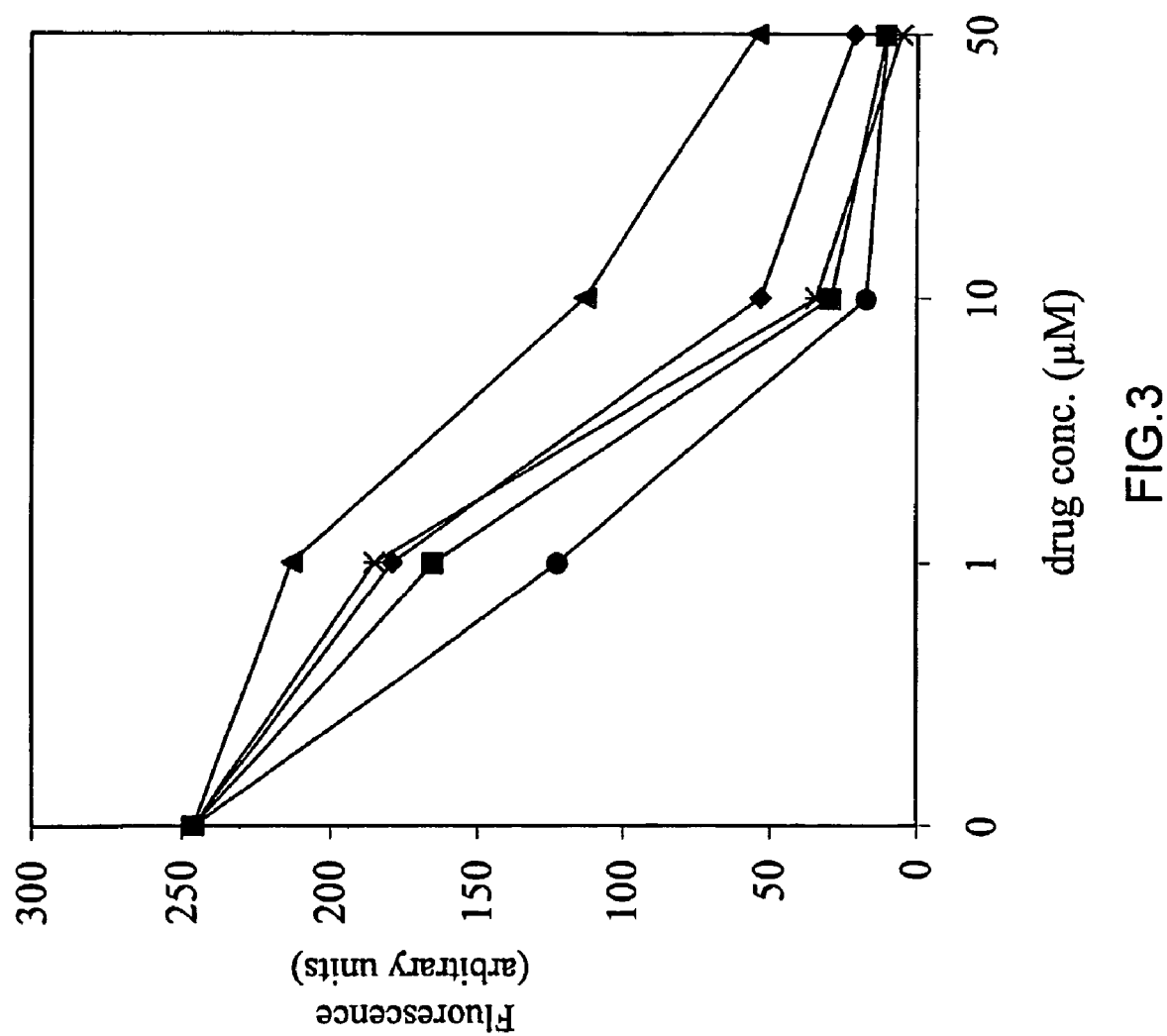
FIG. 3 shows the dependence of EtBr fluorescence on different concentrations of DNA modified by cisplatin (-|-); transplatin (-^-); trans-[PtCl$_2$(NH$_3$)(piperazine)].HCl (-|-); trans-[PtCl$_2$(4-picoline)(piperazine)].HCl (-x-) and trans-[PtCl$_2$(NH$_3$)(piperidino-piperidine)].HCl (-?-). Data points were measured in triplicate which varied on average by ±3%.

The formation of calf thymus DNA platination was also examined. To this end, calf thymus DNA was incubated with different compounds (Table 3) in which the following parameters were determined:

was formed with trans-[PtCl$_2$(NH$_3$)(piperidino-piperidine)].HCl (Table 4 and also in FIG. 3).

TABLE 4

Penetration and formation of Pt-DNA adducts of various platinum complexes

| Name | Penetration to cells (pmol Pt/1 * 10$^6$ cells) 24 hr | | Pt-DNA adducts (pmol Pt/50 µg 24 hr DNA) | |
|---|---|---|---|---|
| | C-26 | OV-1063 | C-26 | OV-1063 |
| cis-DDP | 2244 | 194 | 149 | 107 |
| trans-DDP | 384 | 474 | 0 | 0 |
| trans-[PtCl$_2$(4-pic)(pip)] | 14974 | 2092 | 51 | 41 |
| trans-[PtCl$_2$(4-pic)(pz)].HCl | 54461 | 12307 | 297 | 205 |

The conclusion thus drawn was that trans-[PtCl$_2$(4-picoline)(piperidine) forms monofunctional and also bifunctional adducts that are capable of inhibiting the intercalation of EtBr into the DNA and, therefore, decreasing of EtBr fluorescence intensity.

TABLE 3

DNA binding

| | t$_{1/2}$ | ΔΔϵmax, | ΔT$_m$ (0.C), r$_b$ = 0.05 | | % IEC/ |
|---|---|---|---|---|---|
| | (min) | r$_b$ = 0.05 | 0.01M Na$_+$ | 0.2 M | unwinding | adduct |
| cis-[PtCl$_2$(NH$_3$)(pip)] | 113 | 0.93 | −2.5 | −6.0 | 13.2° | 5 |
| Cis-[PtC$_2$(NH$_3$)(pz)] | 35 | | 3.5 | −4.5 | 13° | 6 |
| trans-[PtCl$_2$(NH$_3$)(pip)] | 113 | 0.15 | +7.6 | −1.9 | 52.8° | 26 |
| trans-[PtCl$_2$(NH$_3$)(pz)] | 20 | 0.01 | 6.3 | −1.9 | 26.4° | 13 |
| trans-[PtCl$_2$(4-pic)(pip)] | 260 | 0.04 | +5.5 | +0.5 | 11° | 2 |
| trans-[PtCl$_2$(4-pic)(pz)] | 12 | −0.30 | +4.7 | −3.5 | 17° | 6 |
| cis-[PtCl$_2$(NH$_3$)(pic)] | 21 | 0.92 | +1.6 | −4.8 | 12° | 4 |
| trans-[PtCl$_2$(NH$_3$)(4-pic)] | 50 | −0.29 | +7.2 | +0.6 | 39.6° | 40 |
| trans-[PtCl$_2$(NH$_3$)$_2$] | 100 | −0.34 | +8.7 | +0.6 | 9.4° | 12 |
| cis-[PtCl$_2$(NH$_3$)$_2$ | 100 | 1.27 | −2.6 | −4.0 | 13° | 6 | t1/2 - half time (in minutes) of the binding of the compounds to calf thymus DNA in 10 mM NaClO$_4$, at 37° C., r$_i$ = 0.08 determined by differential pulse polarography;
Δ$_{Δϵmax}$ - the maximum of the positive CD band at around 275 nm, the difference between the control and platinated calf thymus DNA;
ΔT$_m$ - the difference in the melting temperature of unplatinated and platinated calf thymus DNA;
unwinding - the unwinding angle per adduct;
% IEC/adduct - frequency of interstrand crosslinks.

As can be seen, both piperazine- and piperidine-containing complexes bind to DNA at a significantly higher rate than cisplatin.

Characterization of DNA Adducts by EtBr Fluorescence

EtBr, as the fluorescent probe, was used to distinguish between perturbations induced in DNA by adducts of platinum (II) compounds[14]. Binding of EtBr by intercalation is blocked in a stoichiometric manner by formation of the bifunctional adducts, as of Cis-Pt, which results in a loss of fluorescence intensity. On the other hand, formation of monofunctional adducts results only in a slight decrease of EtBr fluorescence.

Figure 4:
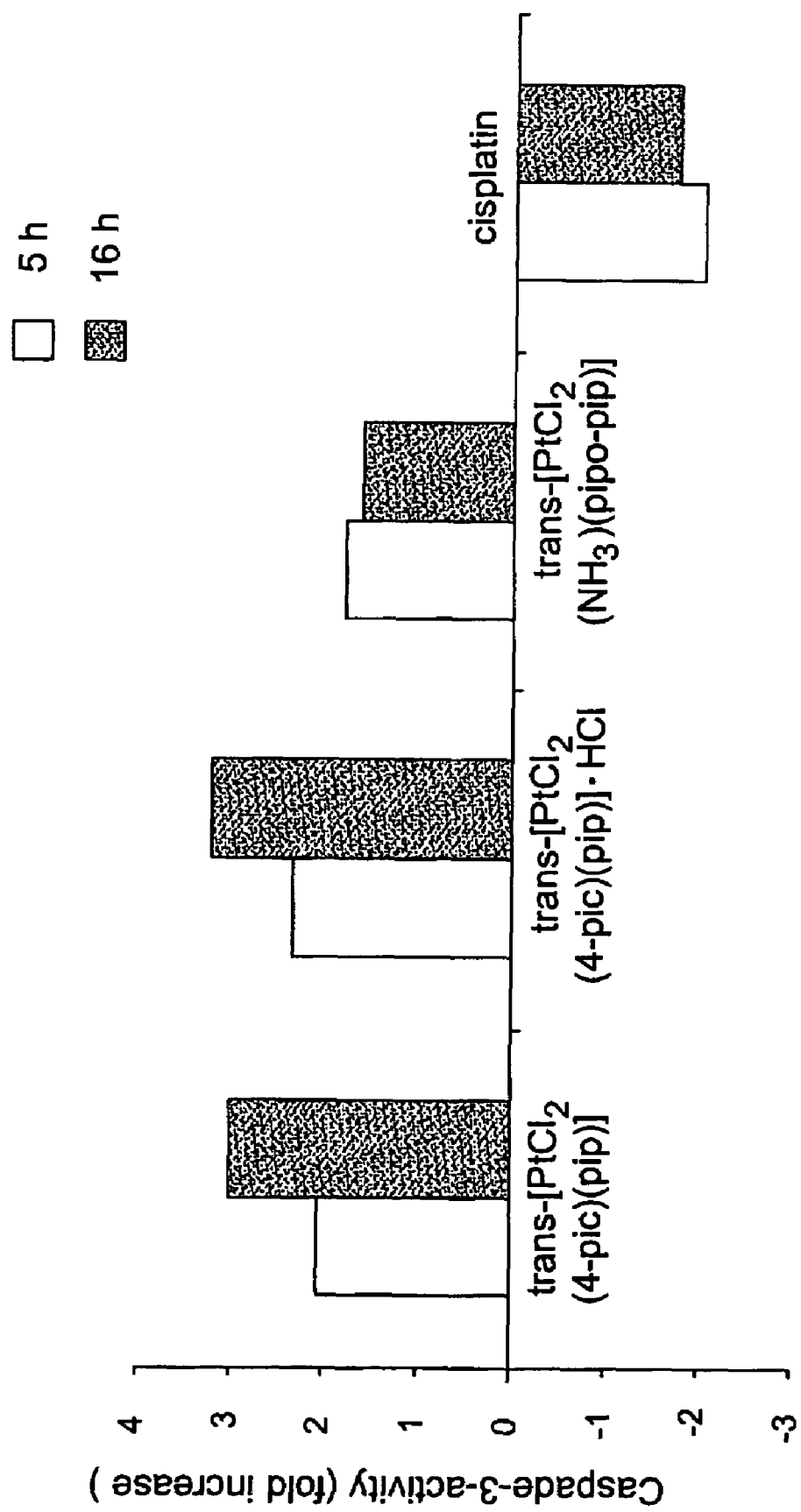
FIG. 4 shows Caspase-3-activity in OV-1063 cells, which were treated with IC$_{50}$ values of trans-[PtCl$_2$(4-picoline)(piperidine)] (6.5 µM, trans-PtCl$_2$(4-pic)(pip)]), trans-[PtCl$_2$(4-picoline)(piperazine)].HCl (7.5 µM or 6.5 µM, respectively, trans-[PtCl$_2$(4-pic)(pz)].HCl), trans-[PtCl$_2$(NH$_3$)(piperidino-piperidine)].HCl (4 µM or 6 µM, respectively, trans-[PtCl$_2$(NH$_3$)(pipo-pip)].HCl) or cisplatin (2 µM or 1 µM, respectively) compared to untreated (control) cells. Both drug-treated and control cells were then harvested, lysed, and assayed after the indicated amount of time, as described in the kit protocol.

DNA platination measurements of DNA modified by trans-[PtCl$_2$(4-picoline) (piperazine)].HCl showed considerable decrease in fluorescence which is in agreement with the formation of bifunctional adducts. On the other hand, the decrease of fluorescence intensity by adducts of trans-[PtCl$_2$(4-picoline)(piperidine)] was lower than that of cisplatin, however, greater than that of transplatin. The best adduct In addition, DNA incubated with trans-[PtCl$_2$(NH$_3$)(piperidino-piperidine)].HCl (3) for 24 hr showed considerable decrease in EtBr fluorescence (slightly higher than that of cisplatin) (FIG. 4). The difference between complex (3) and cis-DDP was higher at low concentration, which suggest that complex (3) posses higher affinity to DNA. The decrease of fluorescence intensity by the adducts of cis-[PtCl$_2$(NH$_3$)(piperaize)].HCl (8) was similar to that of cisplatin (FIG. 4).

Assessment of Apoptosis

Apoptosis, also known as programmed cell death, is involved in the regulation of cell number in multicellular organism, and the pathogenesis of various diseases, including tumor progression, neurodegenerative disorders and viral infections. It has been demonstrated in most cell types that phosphatidylserine (PS), a lipid normally confined to the inner leaflet of the plasma membrane of the normal cell. In the cell that undergoes apoptosis the PS is exported to the outer plasma membrane leaflet in the early stage of apoptosis. PS exposure in treated C-26 and OV-1063 cells was detected by staining with MC 540, which has a strong affinity to PS and chromatin condensation was assessed by staining with DAPI, that preferentially stains double stranded DNA.

Distinguishing features of apoptosis in trans-[PtCl$_2$(4-picoline)(piperidine)] treated OV 1063 cells were observed as evidenced by appearance of red fluorescence in the cell membrane and increasing green fluorescence of nucleus in contrast to red-uncolored untreated cells (results not shown). The results of this staining showed that large proportion of the OV-1063 cells appeared to be apoptotic after 5 hr of treatment with 6.5 μM of trans-[PtCl$_2$(4-picoline)(piperidine)]. The cell surface of C-26 cells became slightly red-fluorescent after 5 hr of treatment with 4.5 μM of trans-[PtCl$_2$(4-picoline)(piperidine)] (results not shown) in contrast to none of the red fluorescence in untreated cells (results not shown).

Recently, members of the caspase (CED-3/ICE) family of proteases have been found to be crucial mediators of the complex biochemical events associated with apoptosis[27]. In particular, the activation of caspase-3, which cleaves a number of different proteins, including poly(ADP-ribose) polymerase (PARP), protein kinase Cδ and actin, has bean shown to be important for the initiation of apoptosis[28]. Thus, activation of caspase-3 was measured in trans-[PtCl$_2$(4-picoline)(piperidine)] treated C-26 and OV-1063 cells. It was found that OV-1063 cells treated for 5 hr with 6.5 μM trans-[PtCl$_2$(4-picoline)(piperidine)] or with 7.5 μM trans-[PtCl$_2$[(4-picoline)(piperazine)].HCl activated caspase-3 (~2-fold increase in fluorescence in treated cells in comparison to untreated cells). Moreover, after 16 hr of treatment of OV-1063 cells with trans-[PtCl$_2$(4-picoline)(piperidine)] or with trans-[PtCl$_2$[(4-picoline)(piperazine)].HCl there was a 3-fold increase in fluorescence in the treated cells in comparison to untreated cells (not shown).

To confirm that the observed fluorescent signal was due to activation of caspase-3, the reversible Ac-DEVD-CHO inhibitor of caspase-3-like proteases was added to the control and treated samples. A drastic decrease in fluorescent signal was found in samples treated with Ac-DEVD-CHO inhibitor (not shown), which argues for specific activation of caspase-3. There was no fluorescent signal found in C-26 cells treated with 4.5 μM trans-[PtCl$_2$(4-picoline)(piperidine)].

To determinate whether OV-1063 or C-26 cells treated with cisplatin undergo apoptosis these cell lines were treated for 5 or 16 hrs with 2 μM or 1.5 μM, respectively. No fluorescent signal was found in cisplatin treated OV-1063 cells or C-26 cells. These findings are in agreement with data of L. Szmigiero et. al. which demonstrated that there is no degraded DNA detected by agarose gel electrophoresis in L1210 cells treated with cisplatin[29]. It was also in agreement with several findings which have shown that colon cancer cells protect themselves by secreting a soluble factor(s) that inhibit apoptosis[30] and by aberrant activation of c-kit which protects colon carcinoma cells from apoptosis.

Protein Binding

Figure 5:
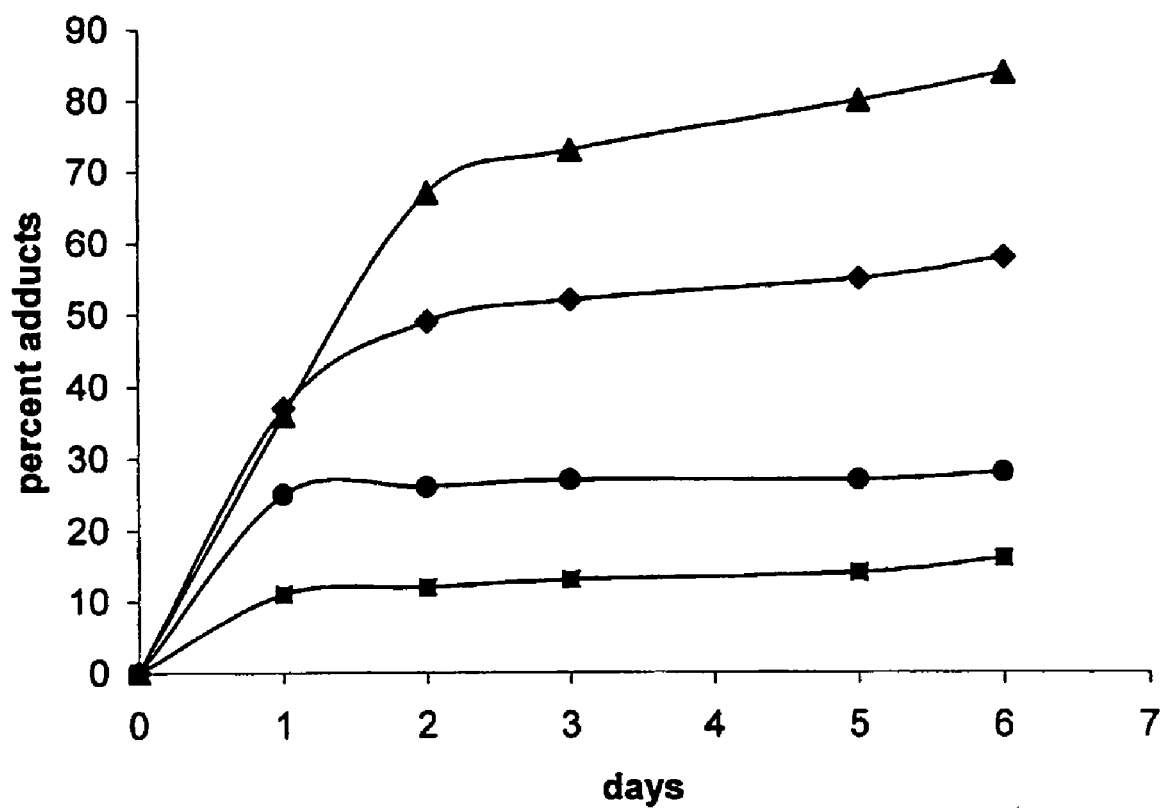
FIG. 5 shows the binding curve of Ubiquitin to cisplatin (-?-); transplatin (-|-); trans-[PtCl$_2$)(NH$_3$)(piperidine)](-^-); and trans-[PtCl$_2$)(NH$_3$)(piperazine)].HCl (-|-).

Since most platinum(II) derivatives which are administered intravenously become protein bound within 24 hr, the binding kinetics of two model proteins, Ubiquitin (MW 8565) and Heart Myoglobin (MW 16951), to Pt complexes was determined. To this end, a 1:1 reaction between the platinum complexes and the proteins were carried out at 1–2 mM concentrations, in 10 mM phosphate buffer, pH 6.4 at 37° C. Protein binding kinetics were measured directly on the reaction mixtures, by Electrospray Ionization Mass Spectrometry (ESI-MS). FIG. 5 shows that while the neutral trans-PtCl$_2$(NH$_3$)(piperidine) binds rapidly to the proteins, followed, with respect to binding rate, by cisplatin and transplatin, the charged piperazine complexes had no significant binding to the proteins. The combination of very rapid binding to DNA with slow and inefficient binding to proteins is a very desirable property of a platinum based anti-tumor drug.

Toxicity

In was found that trans-[PtCl$_2$(NH$_3$)(piperidino-piperidine)].HCl and cis-DDP were non-toxic at concentration of 5 mg/kg, and trans-[PtCl$_2$(4-picoline)(piperazine)].HCl was non-toxic at concentration of 20 mg/kg.

In Vivo Antitumor Effect

Female BALB/C mice (in the weight range of 17–20 gr) were injected i.p. with 1*10$^6$ C-26 colon carcinomas. The viability of these cells was >90% by trypan blue exclusion.

Figure 6:
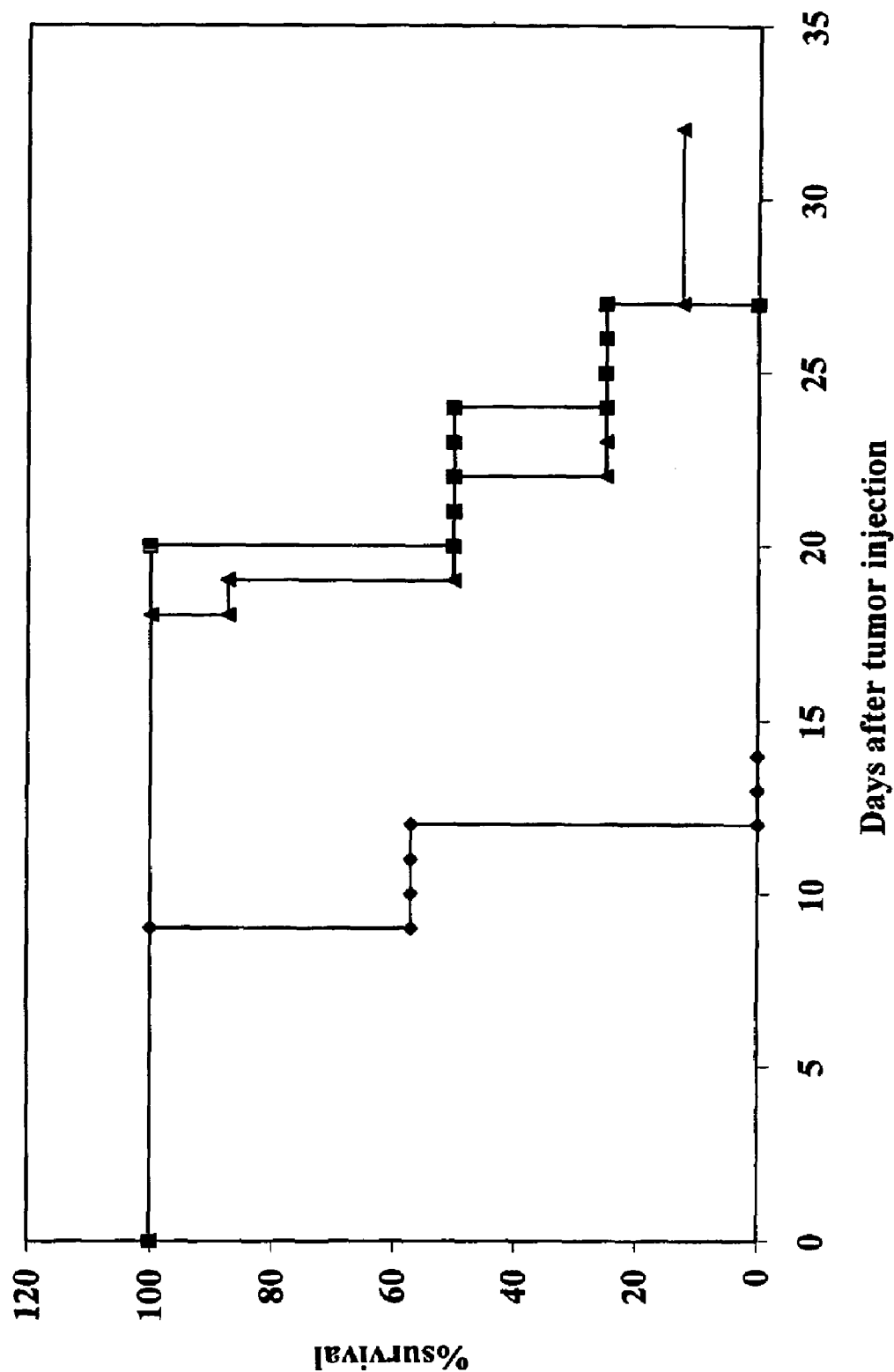
FIG. 6 shows the antitumor activity of trans-[PtCl$_2$(NH$_3$)(piperidino-piperidine)].HCl (-|-) as compared to cis-DDP (-|-) in female BALB/C mice inoculated with C-26 colon carcinoma and treated according to the schedule described herein below.

The therapeutic efficacy of trans-[PtCl$_2$(NH$_3$)(piperidino-piperidine)].HCl was studied and compared to cisplatin. Treatment was as performed according to the schedule described above. The results are presented in Table 5 and in FIG. 6.

TABLE 5

Antitumor effect in first schedule of treatment

| Treatment | Dose (mg/kg) | Dose (mmole/kg) | No. of mice | Survival (days) | Increase in life span (%) |
|---|---|---|---|---|---|
| control | | | 7 | 11.5 ± 0.5 | |
| cisplatin | 5 | 16.6 | 8 | 24 ± 5 | 108 |
| trans-[PtCl$_2$NH$_3$ (pip-pip)].HCl | 5 | 10.3 | 8 | 24 ± 3 | 108 |

EXAMPLE 3

Liposomal Formulation

Preparation and Characterization of Sterically Stabilized Liposomes (SSL) Containing trans-[PtCl$_2$(NH$_3$)(piperidino-piperidine)].HCl Preparation of SSL Containing trans-[PtCl$_2$(NH$_3$) (piperidino-piperidine)].HCl Trans-[PtCl$_2$(NH$_3$)(piperidino-piperidine)].HCl (10 mg/ml) was dissolved in 0.9% NaCl at 65° C. and left at this temperature for 1 hr. Lipids (HSPC:cholesterol:PEG$^{2000}$-DSPE 51:44:5) were dissolved in ethanol. The lipids were hydrated by adding this ethanolic solution to the drug mixture. Final lipid concentration was 150 mg/ml (15%) in 25% ethanol, at 65° C. The mixture was kept stirring for 1 hr at 65° C., then extruded at 65° C., 5 times through 25 mm polycarbonate filters with 200 nm pore size using Lipex extruder (Nothern Lipids Inc, Vancouver, Canada), followed by extrusion 11 times trough a 100 nm pore size polycarbonate filter. Sized liposomes (~100 nm) were allowed to cool to room temperature. During the cooling, a heavy precipitate formed the supernatant was collected. Then supernatant was cooled to 4° C. overnight and the supernatant was collected again. The supernatant was collected and dialyzed against 10 mM histidine buffer (pH=6.5) containing 10% sucrose and 1 mM NaCl for overall of 5 times against 100 vols. of buffer and 1 time against 200 vols at 4° C. Under these conditions, a complete equilibration with buffer should occur. The final liposome dispersion was a translucent white.

Characterization of SSL Containing trans-[PtCl$_2$(NH$_3$)(piperidino-piperidine)].HCl Liposomes were characterized for their size distribution at 25° C. by dynamic light-scattering (DLS) with a Coulter model N4 SD (Coulter Electronics, Hialeah, Fla., USA).

The concentration of the phospholipids (PLs) was checked by lipid phosphorus content (modified Bartlett method)[31].

The platinum concentration in the liposomes was measured by flameless Zeeman atomic absorption spectrometer (FAAS). The platinum concentration was calculated according to a calibration curve included 5 standards of K$_2$PtCl$_4$ stock solution with concentrations ranging from 50 to 250 ng platinum per mL.

The SSL containing trans-[PtCl$_2$(NH$_3$)(piperidino-piperidine)].HCl is characterized by the following parameters: Size—102 nm; Concentration of trans-[PtCl$_2$(NH$_3$)(piperidino-piperidine)].HCl in the formulation: 1 mM; Concentration of the lipid in the formulation: 94 mM; and Percentage of encapsulation (Pt/Pl ratio in liposomes/initial Pt/Pl ratio×100) 8%.

Characterization of Pt Release from trans-[PtCl$_2$(NH$_3$)(piperidino-piperidine)].HCl SSL Sulfur containing glutathion (GSH) is known as strong platinophile. Hence it was chosen for the release experiments of the platinum from the liposome. Its fast reaction with platinum and the strong chemical shift the binding of its sulfur induces on the $^{195}$Pt-NMR will enable us to detect only the diaminedichloroplatinum at the range of interest. An active positively charged derivate was trans-[PtCl$_2$(NH$_3$)(piperidino-piperidine)].HCl (3).

All NMR spectra were recorded on a Varian Inova 500 MHz spectrometer using a 5 mm switchable probe. $^{195}$Pt NMR spectra were referenced externally to K$_2$PtCl$_4$ in HCl (−1624 ppm).

$^{195}$NMR Experiment

To 0.5 mL of the liposome suspension (0.5 mg/mL) in NMR tube, 2 eq. of glutathion (GSH) were added and the suspension was vigorously shacked for 2 min. $^{195}$Pt-NMR test indicated that the complex inside the liposome is intact (δ=−2134.597 ppm). The sample was left at 37° C. $^{195}$Pt-NMR follow up was done after 1, 2, and 7 days. Through the first 2 days the platinum moiety was intact. $^{195}$Pt-NMR that was done at the seventh day revealed the total disappearance of the chemical shift characteristic of the dimminedichloroplatinum(II) moiety.

To evaluate the effect of (GSH) on the release of the platinum drug the above experiment was repeated with no GSH. $^{195}$Pt-NMR revealed that the complex is intact inside even after 10 day at 37° C. (δ=−2132.585 ppm) with minor product at δ=−2661.428 ppm.

In summery the results indicated clearly that the charged complex trans-[PtCl$_2$(NH$_3$)(piperidino-piperidine)].HCl, in contrast to cisplatin is released. The total disappearance of the characteristic chemical shift of the diaminedichloroplatinum(II) means that the ligands in the coordination sphere have changed. Nevertheless, the fact that no change is apparent in the GSH free experiment is not a clue for lack of release. For that the solution out side should be filtered and atomic absorption (AA) and (if possible) $^{195}$Pt-NMR in order to verify the existence of the platinum moiety outside the liposome.

EXAMPLE 4

Bis-platinum Tetra-functional Positively Charged Piperazine-based Complexes

Continuing the efforts to synthesize non-classical platinum complexes, tetrafunctional positively charged bis-platinum complexes was synthesized according to the following scheme:

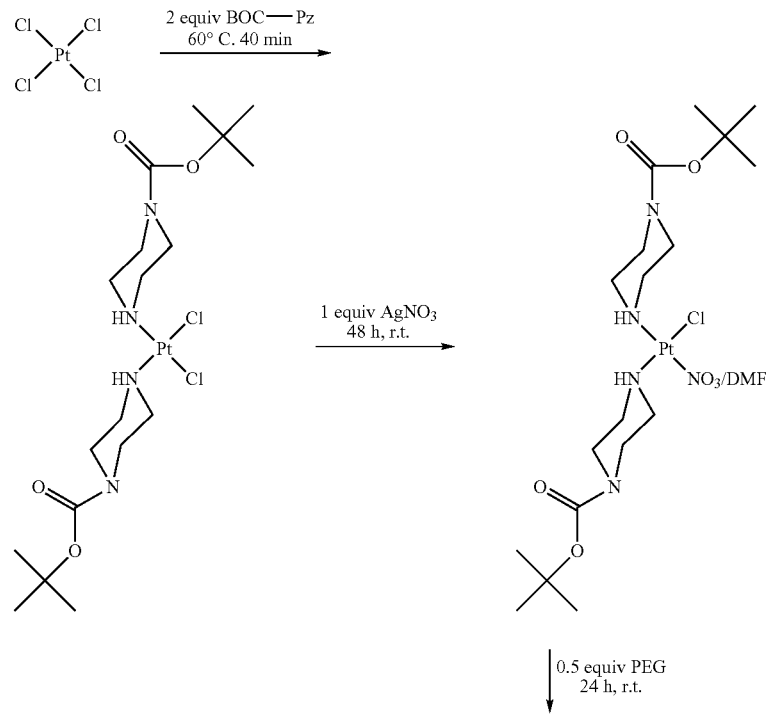

-continued

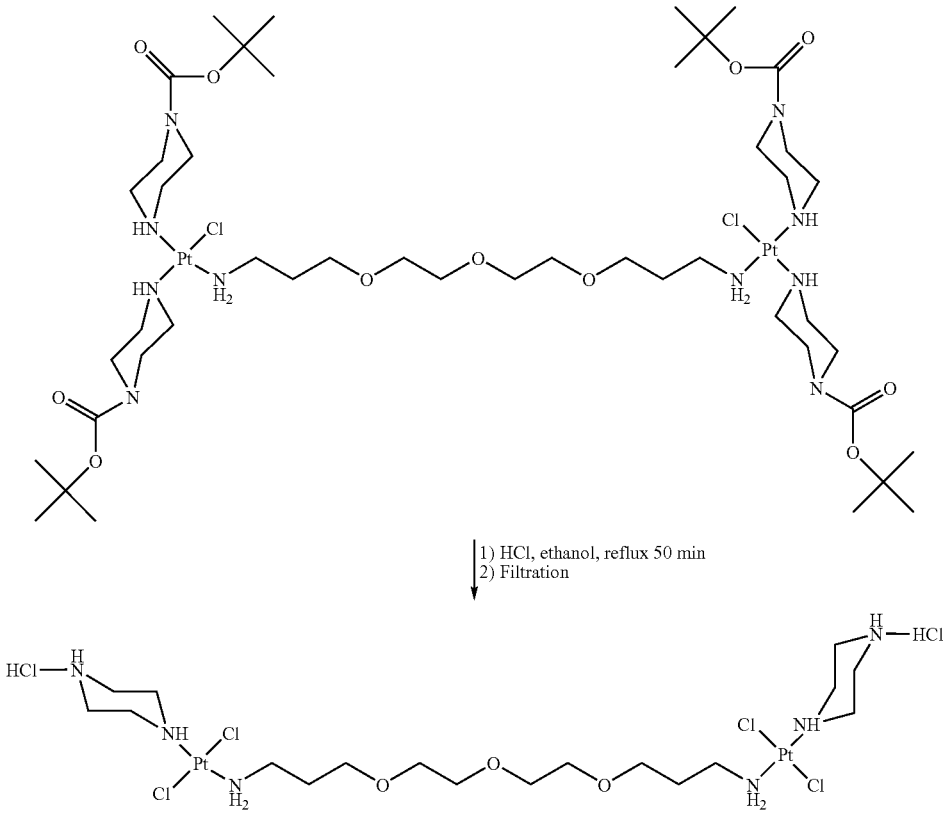

1) HCl, ethanol, reflux 50 min
2) Filtration

Cis-PtCl$_2$(BOC-Pz)$_2$ (1 g, 2.41 mmol) was dissolved in 20 mL DDW. To the stirred mixture, 2 eq. (0.9 g, 4,84 mmol) of tert-butyl 1-piperazine carboxylate were added and the mixture was wormed to 70° C. Stirring and warming continued for 50 min., then yellow precipitate was collected and washed twice with 40 mL DDW. After drying, the yellow product was characterized using $^{195}$Pt-NMR(DMF) and used with no further purification.

$^{195}$Pt-NMR(DMF): δ=−2239.4 ppm, −2267.8 ppm

Synthesis of Bis-[{trans,trans-(PtCl$_2$-Pz)$_2$}(Linker)].2HCl

In dark, cis-PtCl$_2$(Boc-Pz)$_2$ (538 mg, 1 mmol) was dissolve in 50 mL DMF. To the stirred yellow solution, 1 eq. (169.88 mg, 1 mmol) of silver nitrate was added and the mixture was stirred at room temperature for 48 hours. $^{195}$Pt-NMR(DMF) indicated the formation of the mononitrato/DMF mono-chloro diaminoplatinum(II) (δ=−2002.987 ppm, −2123.995) with few traces of the starting material at (δ=−2240.477 ppm) At his stage the AgCl precipitate was filtered off and 0.5 eq. (110 mg, 0.5 mmol) of 4,7,10-trioxa-1,13-tridecanediamine were added. The mixture was stirred at dark overnight. $^{195}$Pt-NMR (DMF) shown the formation of the mono-chloro-triamine platinum (δ=−2542.974 ppm, −2570.911 ppm). The yellowish filtrate was taken and solvents were evaporated under reduced pressure to dryness. The gum was dissolve in 20 ml of ethanol and 1 mL of concentrated hydrochloric acid was added. The mixture was stirred at room temperature until total solubilization, and then temperature was elevated to reflux for 50 minutes. Through out this period of time yellowish precipitate was formed. The reaction mixture was allowed to cool to room temperature and the precipitate was collected, washed with 20 ml ethanol and dried.

$^{195}$Pt-NMR(H$_2$O): δ=−2224.396 ppm, 2238.142 ppm, 2248.194 ppm.

REFERENCES

1) Jamieson, E. R. & Lippard, S. J.; Structure, Recognition, and Processing of Cisplatin-DNA Adducts. *Chem. Rev.* 1999; 99(9); 2467–2498.
2) Kartalou, M. & Essigmann, J. M. Recognition of cisplatin adducts by cellular proteins. *Mutat. Res.* 2001, 478, 1–2, 1–21.
3) Gonzalez, V. M.; Fuertes, M. A.; Alonso C.; Perez J. M. Is cisplatin-induced cell death always produced by apoptosis? *Mol. Pharmacol.* 2001, 59, 4, 657–63.
4) Kartalou M, Essigmann J M. Mechanisms of resistance to cisplatin. *Mutat. Res.* 2001, 478, 1–2, 23–43.
5) Cornelison, T. L. & Reed, E. Nephrotoxicity and Hydration Management for Cisplatin, Carboplatin, and Ormaplatin, *Gynecol One.* 1993, 50, 2, 147–158.
6) Wong, E. & Giandomenico, C. M.; Current Status of Platinum-Based Antitumor Drugs *Chem. Rev.* 1999; 99(9); 2451–2466.
7) Cleare, M. J.; Hoeschele, J. D. Studies on the antitumor activity of group VIII transition metal complexes. Part I. Platinum(II) complexes. *Bioniorg. Chem.* 1973, 2,187–210.
8) Bierbach, U.; Qu, Y.; Hambley, T. W.; Peroutka, J.; Nguyen, H. L.; Doedee, M.; Farrell, N.; Synthesis, Structure, Biological Activity, and DNA Binding of Platinum (II) Complexes of the Type trans-[PtCl$_2$(NH$_3$)L]

(L=Planar Nitrogen Base). Effect of L and Cis/Trans Isomerism on Sequence Specificity and Unwinding Properties Observed in Globally Platinated DNA. *Inorg. Chem.* 1999; 38, 15, 3535–3542.
9) Montero, E. I.; Díaz, S.; González-Vadillo, A. M.; Pérez, J. M.; Alonso, C. & Navarro-Ranninger, C. Preparation and characterization of novel trans-[PtCl(2)(amine)(isopropylamine)]compounds: cytotoxic activity and apoptosis induction in ras-transformed cells, *J. Med. Chem.* 1999, 42, 20, 4264–4268.
10) Coluccia, M.; Nassi, A.; Boccarelli, A.; Giordano, D.; Cardellicchio, N.; Locker, D.; Leng, M.; Sivo, M.; Intini, F. P.; & Natile, G. In vitro and in vivo antitumour activity and cellular pharmacological properties of new platinum-iminoether complexes with different configuration at the iminoether ligands, *J. Inorg. Biochem.* 1999, 77, 1–2, 31–35.
11) John D. Roberts, John Peroutka and Nicholas Farrell Cellular pharmacology of polynuclear platinum anti-cancer agents, *J. Inorg. Biochem.* 1999, 77, 1–2, 51–57.
12) Kelland, L. R; Sharp, S. Y.; O'Neill, C. F.; Raynaud, F. I.; Beale, P. J. & Judson, I. Mini-review: discovery and development of platinum complexes designed to circumvent cisplatin resistance, *J. Inorg. Biochem.* 1999, 77, I 1–2, 111–115.
13) Bierbach, U.; Sabat, M.; Farrell, N.; Inversion of the Cis Geometry Requirement for Cytotoxicity in Structurally Novel Platinum(II) Complexes Containing the Bidentate N,O-Donor Pyridin-2-yl-acetate *Inorg. Chem.* 2000; 39(9); 1882–1890.
14) Hollis, L S; Amundsen, A R; Stern, E W. Chemical and biological properties of a new series of cis-diammine-platinum(II) antitumor agents containing three nitrogen donors: cis-[Pt(NH$_3$)$_2$(N-donor)Cl]+, *Journal of Medicinal Chemistry*, Volume 32, Issue 1, January 1989, Pages 128–136.
15) Kelland, L. R.; Abel, G.; McKeage, M. J.; Jones, M.; Goddard, P. M., Valenti, M.; Murrer, B. A., Harrap, K. R. Preclinical antitumor evaluation of bis-acetato-ammine-dichloro-cyclohexylamine platinum(IV): an orally active platinum drug. *Cancer Res.* 1993, 53, 2581–2586.
16) Loh, S. Y.; Mistry, P.; Kelland, L. R.; Abel, G.; Harrap, K. R. Reduced drug accumulation as a major mechanism of acquired resistance to cisplatin in a human ovarian carcinoma cell line: circumvention studies using novel platinum (II) and (IV) ammine/amine complexes. *Brit. J. Cancer.* 1992, 66, 1109–1115
17) Goddard, P. M; Orr, R. M.; Valenti, M. R.; Barnard, C. F.; Murrer, B. A.; Kelland, L. R.; Harrap, K. R. Novel trans-platinum complexes: comparative in vitro and in vivo activity against platinum-sensitive and resistant murine tumours. *Anticancer Res.* 1996, 16,33–8
18) Behrens, B. C.; Hamilton, T. C.; Masuda, H.; Grotzinger, K. R.; Whang-Peng, J.; Louie, K. G.; Knutsen, T.; McKoy, W. M.; Young, R. C.; Ozols, R. F. Characterization of a cis-diamminedichloroplatinum(II)-resistant human ovarian cancer cell line and its use in evaluation of platinum analogues. *Cancer Res.* 1987, 47, 414–418.
19) Gorodetsky, R.; Levy-Acaba, F.; Mou, X,; Vexter, A. M. Combination of cisplatin and radiation in cell culture: effect of duration of exposure to drug and timing of irradiation. *Int. J. Cancer* 1998, 75, 635–642.
20) Gorodetsky, R.; Moy, X.; Pfeffer, M. R.; Peretz, T.; Levy-Agababa, F.; Vexler, A. M. Sub-additive effect of the combination of radiation and cisplatin in cultured murine and human cell lines. *Isr. J. Med. Sci.* 1995, 31, 175–180.
21) Cory, A H; Owen, T C; Barltrop, J A; Cory, J G Use of an aqueous soluble tetrazolium/formazan assay for cell growth assays in culture, *Cancer Communications*, Volume 3, Issue 7, July 1991, Pages 207–212 Lindauer, E.; Holler, E. Cellular distribution and cellular reactivity of platinum(II) complexes. *Biochem. Pharmacol.* 1996, 52, 7–14.
22) Zuidan, N. J.; Hirsh-Lerner, D.; Margulies, S.; Barenholz, Y. Lamellarity of cationic liposomes and mode of preparation of lipoplexes affect transfection is efficiency. *Biochim. Biophy.s Acta* 1999, 1419, 207–220.
23) Even-Chen, S,; Barencholz, Y. DOTAP cationic liposomes prefer relaxed over supercoiled plasmide *Boichim. Biophys. Acta* 2000, 1509, 176–188.
24) Reid, S.; Cross, R.; Snow, E. C. Combined Hoechst 33342 and merocyanine 540 staining examine murine B cell cycle stage, viability and apoptosis. *J. Immunol. Methods* 1996, 192, 43–54.
25) Holford, J; Raynaud, F.; Murrer, B. A.; Grimaldi, K; Hartley, J. A.; Abrams, M; Kelland, L. R. Chemical, biochemical and pharmacological activity of the novel sterically hindered platinum co-ordination complex, cis-[amminedichloro(2-methylpyridine)]platinum(II) (AMD473), *Anti-Cancer Drug Des.* 1998, 13, 1,1–18.
26) Thornberry, N. A.; Lazebnic, Y. Caspases: enemies within. *Science* 1998, 281, 1312–1316.
27) Villa, P.; Kaufmann, S. H.; Earnshaw, W. C. Caspases and caspase inhibitors. *Trends Biochem. Sci.* 1997, 22, 388–393.
28) Ciesielska, E.; Studzan, K.; Zyner, E.; Ochocki, J.; Szmigiero, L. DNA damage and apoptosis induction in L1210 cells by diamminedichloroplatinum(II) and its new aminoflavone analogue *Cell. Mol. Biol. Lett.* 2000, 5, 441–450.
29) Liu, W.; Davis, D. W.; Ramirez, K.; McConkey, D. J.; Ellis, L. M. Endothelial cell apoptosis is inhibited by a soluble factor secreted by human colon cancer cells. *Int. J. Cancer* 2001, 92, 26–30.
30) Y. Barenholz, S. Amsalem. In: Liposome Technology 2$^{nd}$ Edn., G. Gregoriadis (Ed.) CRC Press, Boca Raton, 1993, vol. 1, pp: 527–616.

The invention claimed is:

1. A platinum complex in trans configuration, the complex having the general formula (I):

$$[Pt(X)(Y)(Am_1)(Am_2)] \qquad (I)$$

wherein:
  X and Y, which may be the same or different, represent a halogen, carboxylate, phosphate or sulphate group;
  Am$_1$ represents an amine selected from ammonia, a primary amine, a secondary amine, a non-planar heterocyclic aliphatic amine or a heterocyclic aromatic amine; and
  Am$_2$ represents a non-planar heterocyclic aliphatic amine;
provided that trans-[Pt(piperidine)$_2$Cl$_2$] and trans-[Pt(morpholine)$_2$Cl$_2$] are excluded.

2. The complex of claim 1, in the form of a dimer in which each monomeric unit is a Pt-complex as defined in claim 1, bound to the other Pt-complex, independently, through the Am$_1$ or through the Am$_2$ or through a linker connected to said Am$_1$ or Am$_2$.

3. The complex of claim 1, wherein said X and Y are the same or different and represent chloride or iodide.

4. The complex of claim 1, wherein said X and Y both represent a chloride.

5. The complex of claim 1, wherein said Am$_1$ represents ammonia.

6. The complex of claim 1, wherein said Am$_1$ represents a primary amine selected from methylamine, ethylamine, n-propylamine, isopropylamine, n-butylamine, n-hexylamine, n-heptylamine or n-nonylamine.

7. The complex of claim 1, wherein said $Am_1$ represents a secondary amine selected from dimethylamine, diethylamine, dipropylamine, dibutylamine.

8. The complex of claim 1, wherein said $Am_1$ represents a non-planar heterocyclic aliphatic amine selected from, piperazine, 2-methylpiperazine, piperidine, 2-, 3-, or 4-hydroxypiperidine, 4-piperidino-piperidine, pyrrolidine, 4-(2-hydroxyethyl)piperazine and 3-aminopyrolidine.

9. The complex of claim 1, wherein said $Am_1$ represents a heterocyclic aromatic amine selected from pyridine, 2-, 3-, 4-aminopyridine, 2-, 3-, or 4-picoline, quinoline, 3-, or 4-aminoquinoline, thiazole, imidazole, 3-pyrroline, pyrazine, 2-methylpyrazine, 4-aminoquinaldine.

10. The complex of claim 1, wherein said $Am_2$ represents a non-planar heterocyclic amine selected from piperazine, 2-methylpiperazine, piperidine, 2-, 3-, or 4-hydroxypiperidine, 4-piperidino-piperidine, pyrrolidine, 4-(2-hydroxyethyl)piperazine and 3-aminopyrolidine.

11. The complex of claim 1, selected from
trans-$[PtCl_2(NH_3)(piperidine)]$;
trans-$[PtCl_2(NH_3)(4-hydroxypiperidine)]$;
trans-$[PtCl_2(NH_3)(4-piperidino-piperidine)]$;
trans-$[PtCl_2(NH_3)(4,4'-bipiperidine)]$;
trans-$[PtCl_2(4-picoline)(piperidine)]$;
trans-$[PtCl_2(NH_3)(piperazine)].HCl$;
trans-$[ptcl_2(isopropylamine)(piperazine)].HCl$;
trans-$[PtCl_2(n-butylamine)(piperazine)].HCl$;
trans-$[PtCl_2(n-nonylamine)(piperazine)].HCl$
trans-$[PtCl_2(piperidine)(piperazine)].HCl$;
trans-$[PtCl_2(4-picoline)(piperazine)].HCl$;
trans-$[PtCl_2(piperazine)(piperazine)].HCl$;
trans-$[PtCl_2(NH_3)[4-(2-hydroxyethyl)piperazine)].HCl$.

12. The complex of claim 1, being positively charged.

13. The complex of claim 2, wherein said linker comprises 4,7,10-trioxa-1,13-tridecane chain.

14. The complex of claim 12, being Bis-[{trans, trans-$(PtCl_2$piperazine$)_2$}(4,7,10-trioxa-1,13-tridecanediamine)].2HCl.

15. A pharmaceutical composition comprising a pharmaceutically acceptable carrier and as an active ingredient a therapeutically effective amount of a platinum (Pt) complex in the trans configuration, the complex having the general formula:

$$[Pt(X)(Y)(Am_1)(Am_2)] \quad (I)$$

wherein
X and Y, which may be the same or different, represent a halogen, carboxylate, phosphate or sulphate group;
$Am_1$ represents an amine selected from ammonia, a primary amine, a secondary amine, a non-planar heterocyclic aliphatic amine or a heterocyclic aromatic amine; and
$Am_2$ represents a non-planar heterocyclic aliphatic amine,
provided that trans-$[Pt(piperidine)_2Cl_2]$ and trans-$[Pt(morpholine)_2Cl_2]$ are excluded.

16. The composition of claim 15, wherein the active ingredient is said Pt complex in a form of a dimer in which each monomeric unit is a Pt-complex bound to the other Pt-complex, independently, trough the $Am_1$ or through the $Am_2$ or trough a linker connected to said $Am_1$ or $Am_2$.

17. The composition of claim 15, wherein the active ingredient is said Pt complex in which X and Y are the same or different and represent chloride or iodide.

18. The composition of claim 17, wherein the active ingredient is said Pt complex in which X and Y both represent a chloride.

19. The composition of claim 15, wherein the active ingredient comprises said Pt complex in which said $Am_1$ represents ammonia.

20. The composition of claim 15, wherein the active ingredient comprises said Pt complex in which $Am_1$ represents a primary amine selected from methylamine, ethylamine, n-propylamine, isopropylamine n-butylamine, n-hexylamine, n-heptylamine or n-nonylamine.

21. The composition of claim 15, wherein the active ingredient comprises said Pt complex in which $Am_1$ represents a secondary amine selected from dimethylamine, dimethylamine, dipropylamine, dibutylamine.

22. The composition of claim 15, wherein the active ingredient comprises said Pt complex in which $Am_1$ represents a heterocyclic aromatic amine selected from pyridine, 2-, 3-, or 4-aminopyridine, 2-, 3-, or 4-picoline, quinoline, 3-, or 4-aminoquinoline, thiazole, imidazole, 3-pyrroline, pyrazine, 2-methylpyrazine 4-aminoquinaldine.

23. The composition of claim 15, wherein the active ingredient comprises said Pt complex in which $Am_1$ represents a non-planar heterocyclic aliphatic amine selected from piperazine, 2-methylpiperazine, 2-pyrazoline, piperidine, 2-, 3-, or 4-hydroxypiperidine, 4-piperidino-piperidine, pyrrolidine, 4-(2-hydroxyethyl)piperazine or 3-aminopyrolidine.

24. The composition of claim 15, wherein the active ingredient comprises said Pt complex in which $Am_2$ is a non-planar heterocyclic aliphatic amine selected from piperazine, 2-methylpiperazine, 2-pyrazoline, piperidine, 2-, 3-, or 4-hydroxypiperidine, 4-piperidino-piperidine, pyrrolidine, 4-(2-hydroxyethyl)piperazine or 3-aminopyrolidine.

25. The composition of claim 15, wherein said active ingredient is selected from
trans-$PtCl_2(NH_3)(piperidine)$];
trans-$[PtCl_2(NH_3)(4-hydroxypiperidine)]$;
trans-$[PtCl_2(NH_3)(4-piperidino-piperidine)]$;
trans-$[PtCl_2(NH_3)(4,4'-bipiperidine)]$;
trans-$[PtCl_2(4-picoline)(piperidine)]$;
trans-$PtCl_2(NH_3)(piperazine)].HCl$;
trans-$[ptcl_2(isopropylamine)(piperazine)].HCl$;
trans-$[PtCl_2(n-butylamine)(piperazine)].HCl$;
trans-$[PtCl_2(n-nonylamine)(piperazine)].HCl$
trans-$[PtCl_2(piperidine)(piperazine)].HCl$;
trans-$[PtCl_2(4-picoline)(piperazine)].HCl$;
trans-$[PtCl_2(piperazine)(piperazine)].HCl$;
trans-$[PtCl_2(NH_3)[4-(2-hydroxyethyl)piperazine)].HCl$.

26. The composition of claim 16, wherein said active ingredient is said dimmer in which the linker comprises a 4,7,10-trioxa-1,13-tridecane chain.

27. The composition of claim 26, wherein said active ingredient is Bis-[{trans, trans-$(PtCl_2$piperazine$)_2$}(4,7,10-trioxa- 1,13-tridecanediamine)]2HCl.

28. The composition of claim 15, wherein said active ingredient is loaded onto liposomes.

29. The composition on of claim 25, wherein said active ingredient is loaded onto liposomes.

30. A method for achieving a therapeutic effect, the method comprising administering to a subject in need an amount of a Pt-complex in trans configuration, the amount being sufficient for achieving said therapeutic effect and the Pt complex has the general formula (I):

$$[Pt(X)(Y)(Am_1)(Am_2)] \quad (I)$$

wherein:
X and Y, which may be the same or different, represent a halogen, carboxylate, phosphate or sulphate group;

Am₁ represents an amine selected from ammonia, a primary amine, a secondary amine, a non-planar heterocyclic aliphatic amine or a heterocyclic aromatic amine; and Am₂ represents a non-planar heterocyclic aliphatic amine, provided that trans- [Pt(piperidine)₂Cl₂] and trans- [Pt(morpholine)₂Cl₂] are excluded.

31. The method of claim 30, wherein said Pt-complex is in a form of a dimer in which each monomeric unit is a Pt-complex bound to the other complex, independently, through the Am₁, through the Am₂ or through a linker connected to said Am₁ or Am₂.

32. The method of claim 30, wherein said subject is administered with a Pt complex in which X and Y are the same or different and represent chloride or iodide.

33. The method of claim 30, wherein X and Y both represent a chloride.

34. The method of claim 30, wherein said subject is administered with a Pt complex in which Am₁ represents ammonia.

35. The method of claim 30, wherein said subject is administered with a Pt complex in which Am₁ represents a primary amine selected from methylamine, ethylamine, n-propylamine, isopropylamine, n-butylamine, n-hexylamine, n-heptylamine or n-nonylamine.

36. The method of claim 30, wherein said subject is administered with a Pt complex in which Am₁ represents a secondary amine selected from dimethylamine, diethylamine, dipropylamine, dibutylamine.

37. The method of claim 30, wherein said subject is administered with a Pt complex in which Am₁ represents a heterocyclic aromatic amine selected from pyridine, 2-, 3- or 4-picoline, quinoline, 3- or 4-aminoquinoline, thiazole, 2-, 3- or 4-aminopyridine, imidazole, 3-pyrroline, pyrazine, 2-methylpyrazine or 4-aminoquinaldine.

38. The method of claim 30, wherein said subject is administered with a Pt complex in which Am₁ represents a non-planar heterocyclic amine selected from piperazine, 2-methylpiperazine, piperidine, 2-, 3-, or 4-hydroxypiperidine, 4-piperidino-piperidine, pyrrolidine, 4-(2-hydroxyethyl)piperazine or 3-aminopyrolidine.

39. The method of claim 30, wherein Am₂ represents a non-planar heterocyclic amine selected from piperazine, 2-methylpiperazine, piperidine, 2-, 3-, or 4-hydroxypiperidine, 4-piperidino-piperidine, pyrrolidine, 4-(₂-hydroxyethyl)piperazine or 3-aminopyrolidine.

40. The method of claim 30, comprising administering to said subject a platinum complex selected from:
trans-[PtCl₂(NH₃)(piperidine)];
trans-[PtCl₂(NH₃)(4-hydroxypiperidine)];
trans-[PtCl₂(NH₃)(4-piperidino-piperidine)];
trans-[PtCl₂(NH₃)(1,4'-bipiperidine)];
trans-[PtCl₂(4-picoline)(piperidine)];
trans-[PtCl₂(NH₃)(piperazine)].HCl;
trans-[ptcl₂(isopropylamine)(piperazine)].HCl;
trans-[PtCl₂(n-butylamine)(piperazine)].HCl;
trans-[PtCl₂(n-nonylamine)(piperazine)].HCl
trans-[PtCl₂(piperidine)(piperazine)].HCl;
trans-[PtCl₂(4-picoline)(piperazine)].HCl;
trans-[PtCl₂(piperazine)(piperazine)].HCl;
trans-[PtCl₂(NH₃) [4-(2-hydroxyethyl)piperazine)].HCl.

41. The method of claim 31, wherein said linker comprises a 4,7,10-trioxa- 1,13-tridecane chain.

42. The method of claim 41, wherein the subject is administered with a therapeutically effective amount of Bis-[{trans, trans-(PtCl₂piperazine)₂}(4,7,10-trioxa-1,13-tridecanediamine)].2HCl.

43. The method of claim 30, for achieving a therapeutic effect, the therapeutic effect comprises forming an adduct between said Pt complex and DNA.

44. The method of claim 31, for achieving a therapeutic effect, the therapeutic effect comprises, forming an adduct between said Pt complex and DNA.

45. The method of claim 30, for achieving a therapeutic effect, the therapeutic effect comprises inhibiting undesired cell proliferation.

46. The method of claim 31, for achieving a therapeutic effect, the therapeutic effect comprises inhibiting undesired cell proliferation.

47. The method of claim 45 for inducing apoptosis of undesired cells.

48. The method of claim 46 for inducing apoptosis of undesired cells.

49. The method of claim 30, wherein said Pt complex is loaded onto a liposome.

50. The method of claim 31, wherein said Pt complex is loaded into a liposome.

51. A platinum complex of the general formula (I):

$$[Pt(X)(Y)(Am_1)(Am_2)] \quad (I)$$

wherein:
X and Y, which may be the same or different, represent a halogen, carboxylate, phosphate or sulphate group;

Am₁ represents an amine selected from ammonia, a primary amine, a secondary amine, a non-planar heterocyclic aliphatic amine or a heterocyclic aromatic amine; and Am₂ represents a non-planar heterocyclic aliphatic amine; provided that the following compounds are excluded:

cis-[PtCl₂(quinoline)(piperidine)];
cis-[PtCl₂(piperidine)(pyridine)];
cis-[PtCl₂-(piperidine)(o-CH₃—C₆H₄—NH₂)];
cis-[PtCl₂(piperidine)(p-CH₃—C₆H₄—NH₂)];
cis-[PtCl₂(morpholine)(pyridine)];
cis-[PtCl₂(morpholine)(o-CH₃—C₆H₄—NH₂)];
cis-[PtCl₂(morpholine)(p-CH₃—C₆H₄—NH₂];
cis-[PtCl₂(piperidine)(aniline)];
cis-[PtCl₂(piperidine)(o-CH₃O—C₆H₄—NH₂)];
cis-[PtCl₂(piperidine)(p-C₂H₅OC₆H₄—NH₂)];
cis-[PtCl₂(quinoline)(cyclohexylamine)];
cis-[PtCl₂(quinoline)(morpholine)];
cis-[PtCl₂(quinoline)(piperidine)];
cis-[PtBr₂(piperazine)(piperazine),
cis-[PtCl₂(piperazine)(piperazine)];
cis-[PtCl₂(piperidine)(piperidine)];
cis-[PtCl₂(morpholie)(morpholine)];
cis-[PtCl₂(pyrrolidine)(NH₃)],
cis-[PtI₂(pyrrolidine)(NH₃)],
cis-{PtICl₂(pyrrolidine)(NH₃)],
cis-[PtCl₂(piperidine)(NH₃)],
cis-[PtI₂(piperidine)(NH₃)],
cis-[PtCl₂(piperidone)(NH₃)],
cis-[PtI₂(piperidone)(NH₃)],
cis-[PtICl(piperidone)(NH₃)],
cis-[PtCl₂(3-hydroxypyrrolidine(NH₃)],
cis-[PtI₂(3-hydroxypyrrolidine)(NH₃)],
cis-[PtClI(3-hydroxypyrrolidine)(NH₃),
trans-[Pt(piperidine)₂Cl₂]; and
trans-[Pt(morpholine)₂Cl₂].

* * * * *

UNITED STATES PATENT AND TRADEMARK OFFICE
CERTIFICATE OF CORRECTION

PATENT NO.        : 7,122,668 B2                                    Page 1 of 1
APPLICATION NO.   : 10/487154
DATED             : November 7, 2006
INVENTOR(S)       : Barenholz et al.

It is certified that error appears in the above-identified patent and that said Letters Patent is hereby corrected as shown below:

Face Page, Please insert:
-- (60) Provisional application No. 60/314,115, filed on August 23, 2001 --

Claim 14, Column 29, Line 36,
Please delete " claim 12" and
replace with -- claim 13 --

Claim 29, Column 30, Line 56,
Please delete "on"

Signed and Sealed this

Sixth Day of March, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,122,668 B2 | Page 1 of 1 |
| APPLICATION NO. | : 10/487154 | |
| DATED | : October 17, 2006 | |
| INVENTOR(S) | : Barenholz et al. | |

It is certified that error appears in the above-identified patent and that said Letters Patent is hereby corrected as shown below:

Face Page, Please insert:
-- (60) Provisional application No. 60/314,115, filed on August 23, 2001 --

Claim 14, Column 29, Line 36,
Please delete " claim 12" and
replace with -- claim 13 --

Claim 29, Column 30, Line 56,
Please delete "on"

This certificate supersedes Certificate of Correction issued March 6, 2007.

Signed and Sealed this

Twenty-seventh Day of March, 2007

JON W. DUDAS
*Director of the United States Patent and Trademark Office*